(12) United States Patent
Ochiya et al.

(10) Patent No.: US 11,965,887 B2
(45) Date of Patent: Apr. 23, 2024

(54) METHOD OF EXAMINING POSSIBILITY OF SUBJECT HAVING PANCREATIC CANCER

(71) Applicant: THEORIA Science Inc., Tokyo (JP)

(72) Inventors: Takahiro Ochiya, Tokyo (JP); Yusuke Yoshioka, Tokyo (JP)

(73) Assignee: THEORIA Science Inc., Tokyo (JP)

( * ) Notice: Subject to any disclaimer, the term of this patent is extended or adjusted under 35 U.S.C. 154(b) by 780 days.

(21) Appl. No.: 16/476,921

(22) PCT Filed: Jul. 10, 2017

(86) PCT No.: PCT/JP2017/025115
§ 371 (c)(1),
(2) Date: Jul. 10, 2019

(87) PCT Pub. No.: WO2018/131192
PCT Pub. Date: Jul. 19, 2018

(65) Prior Publication Data
US 2019/0331685 A1 Oct. 31, 2019

(30) Foreign Application Priority Data

Jan. 12, 2017 (JP) .................................. 2017-003709

(51) Int. Cl.
*G01N 31/00* (2006.01)
*C12N 15/09* (2006.01)
*G01N 33/53* (2006.01)
*G01N 33/574* (2006.01)

(52) U.S. Cl.
CPC ....... *G01N 33/57438* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 2009/0162361 A1* | 6/2009 | Nakamura | C12Q 1/6886 435/7.1 |
| 2009/0220944 A1* | 9/2009 | Fais | G01N 33/5743 435/5 |
| 2010/0196426 A1* | 8/2010 | Skog | C12N 15/1017 604/7 |
| 2015/0017660 A1 | 1/2015 | Ochiya | |
| 2016/0047812 A1 | 2/2016 | Ohta et al. | |

FOREIGN PATENT DOCUMENTS

| | | | |
|---|---|---|---|
| WO | WO-2005/101001 A2 | 10/2005 | |
| WO | WO-2005101001 A2 * | 10/2005 | ........... G01N 33/574 |
| WO | WO-2013/094307 A1 | 6/2013 | |
| WO | WO-2014/167969 A1 | 10/2014 | |

OTHER PUBLICATIONS

Khorana et al. Journal of Clinical Oncology, vol. 34, No. 21, Jul. 20, 2016, pp. 2541-2556 (Year: 2016).*
Mendt et al. (JCI Insight, 2018, vol. 3, No. 8, e99263, pp. 1-22) (Year: 2018).*
Taylor, Douglas D., et al., Gynecologic Oncol, 110 (2008) pp. 13-21.
Yoshioka, Yusuke et al., "Circulating cancer-associated extracellular vesicles as early detection biomarkers for pancreatic ductal adenocarcinoma," the 36th Japan Society for Molecular Tumor Marker Research Program Koen Shoroku, pp. 70-71, Sep. 12, 2016.
Somiya, Masaharu et al., "Kecchu Exosome ni yoru Gan Shindan no Kanosei," Hematology Frontier, vol. 26, No. 10, pp. 1379-1384, Sep. 30, 2016.
International Search Report dated Oct. 10, 2017 for PCT/JP2017/025115.
Extended European Search Report dated Oct. 22, 2020 in European Patent Application No. 17891449.5.
Takahiro Ochiya, "Practical application of novel body fluid diagnosis using cancer specific exosomes," Project for Cancer Research and Therapeutic Evolution, 2017, pp. 1-5.
Takamitsu Sano et al., "Comparative characterization of GPRC5B and GPRC5C LacZ knockin mice; behavioral abnormalities in GPRC5B-deficient mice," Biochemical and Biophysical Research Communications, 2011, vol. 412, No. 3, pp. 460-465.

* cited by examiner

*Primary Examiner* — Lisa V Cook
(74) *Attorney, Agent, or Firm* — Faegre Drinker Biddle & Reath LLP

(57) ABSTRACT

A method of examining a possibility of a subject having pancreatic cancer, including measuring GPRC5C (G protein-coupled receptor family C group 5 member C) present in an exosome in a specimen collected from the subject.

6 Claims, 2 Drawing Sheets

METHOD OF EXAMINING POSSIBILITY OF SUBJECT HAVING PANCREATIC CANCER

TECHNICAL FIELD

The present invention relates to a method of examining a possibility of a subject having pancreatic cancer, a method of distinguishing pancreatic cancer from a pancreatic disease other than pancreatic cancer, a method of monitoring a possibility of a subject having pancreatic cancer, a reagent for examining a possibility of a subject having pancreatic cancer, a reagent for distinguishing pancreatic cancer from a pancreatic disease other than pancreatic cancer, a reagent for monitoring a possibility of a subject having pancreatic cancer, a pancreatic cancer marker, a pancreatic cancer diagnostic reagent, and a method of determining a biological sample.

Priority is claimed on Japanese Patent Application No. 2017-003709, filed on Jan. 12, 2017, the content of which is incorporated herein by reference.

BACKGROUND ART

An exosome is a granular vesicle present in a body fluid in a living body. It is known that, on an exosome surface, similar to a general cell surface, various membrane proteins are present. In addition, it is reported that the exosome is secreted from various cells, for example, cells in immune system or various cancer cells, and attention is paid to the fact that the exosome functions as an intermediate role for intercellular communication in a living body and is associated with physiological phenomenon, and association of the exosome with a disease such as cancer.

In recent years, a method of detecting colorectal cancer by measuring an amount of exosome expressing specific antigens (CD9, CD63, CD147) on an exosome surface (Patent Document 1), an increase of an amount of exosome in blood in accordance with progress of cancer in an ovarian cancer patient (Non-Patent Document 1), and the like have been reported.

In addition, as a method of measuring components present in an exosome, an immunoassay method using a first antibody specifically binding to a first antigen present in the exosome and a second antibody specifically binding to a second antigen present in the exosome is known (Patent Document 2).

GPRC5C (G protein-coupled receptor family C group 5 member C) is a 7-times transmembrane type G protein-coupled receptor, and it is reported that GPRC5C is highly expressed in the endocrine system such as adrenal gland, thyroid, and pancreas, and is used for diagnosis of endocrine diseases (Patent Document 3).

PRIOR ART DOCUMENTS

Patent Documents

[Patent Document 1] PCT International Publication No. WO2014/167969
[Patent Document 2] PCT International Publication No. WO2013/094307
[Patent Document 3] PCT International Publication No. WO2005/101001

Non-Patent Document

[Non-Patent Document 1] Taylor., et al., Gynecologic Oncol, 110 (2008) pp13-21

SUMMARY OF INVENTION

Problems to be Solved by the Invention

An object of the present invention is to provide a method and a reagent for examining a possibility of a subject having pancreatic cancer, a method and a reagent for distinguishing pancreatic cancer from a pancreatic disease other than pancreatic cancer, a method and a reagent for monitoring a possibility of a subject having pancreatic cancer, a pancreatic cancer marker, a pancreatic cancer diagnostic reagent, and a method for determining a biological sample.

Means for Solving the Problems

As a result of intensive studies to solve such a problem, the present inventors found that a possibility of a subject having pancreatic cancer can be determined by measuring GPRC5C, particularly GPRC5C present in an exosome, in a specimen collected from a subject, pancreatic cancer can be distinguished from a pancreatic disease other than pancreatic cancer and a possibility of a subject having pancreatic cancer can be monitored by measuring GPRC5C present in an exosome in a specimen collected from a pancreatic cancer patient and a specimen collected from a pancreatic disease patient other than a pancreatic cancer patient, and thereby completing the present invention. That is, the present invention relates to the following [1] to [53].

[1] A method for examining a possibility of a subject having pancreatic cancer, including measuring GPRC5C present in an exosome in a specimen collected from the subject.

[2] The method according to [1], including the following steps:
(1) a step of collecting a specimen from the subject;
(2) a step of measuring a concentration of GPRC5C present in the exosome in the specimen collected in step (1); and
(3) a step of determining that the possibility of the subject having pancreatic cancer is high in a case where the concentration of GPRC5C measured in step (2) is higher than a concentration of GPRC5C present in an exosome in a specimen collected from a healthy person, and determining that the possibility of the subject having pancreatic cancer is low in a case where the concentration of GPRC5C measured in step (2) is the same as or lower than the concentration of GPRC5C present in the exosome in the specimen collected from the healthy person.

[3] The method according to [2], in which in step (2), measurement of the concentration of GPRC5C present in the exosome in the specimen collected in step (1) is carried out by using an exosome isolated from the specimen.

[4] The method according to [2] or [3], in which step (2) is carried out by an immunoassay method.

[5] The method according to [4], in which the immunoassay method is carried out by using an antibody binding to GPRC5C or a fragment of the antibody.

[6] The method according to [4], in which the immunoassay method is carried out by using an antibody binding to GPRC5C or a fragment of the antibody and an antibody binding to an antigen specifically expressed in an exosome (hereinafter, referred to as exosome-specific antigen) or a fragment of the antibody.

[7] The method according to [6], in which the exosome-specific antigen is CD63, CD9, CD81, CD37, CD53, CD82, CD13, CD11, CD86, ICAM-1 (intercellular adhesion molecule-1), Rab5, Annexin V, or LAMP1 (lysosome-associated membrane protein 1).

[8] The method according to any one of [1] to [7], in which the specimen is blood.

[9] A method for distinguishing pancreatic cancer from a pancreatic disease other than pancreatic cancer in a pancreatic disease patient, including measuring GPRC5C present in an exosome in a specimen collected from a pancreatic disease patient.

[10] The method according to [9], including the following steps:

(1) a step of collecting a specimen from a pancreatic disease patient;

(2) a step of measuring a concentration of GPRC5C present in the exosome in the specimen collected in step (1); and (3) a step of determining that a possibility of the subject having pancreatic cancer is high in a case where the concentration of GPRC5C measured in step (2) is higher than a concentration of GPRC5C present in an exosome in a specimen collected from a patient having a pancreatic disease other than pancreatic cancer, and determining that the possibility of the subject having a pancreatic disease other than pancreatic cancer is high in a case where the concentration of GPRC5C measured in step (2) is the same as or lower than the concentration of GPRC5C present in the exosome in the specimen collected from the patient having a pancreatic disease other than pancreatic cancer.

[11] The method according to [10], in which in step (2), measurement of the concentration of GPRC5C present in the exosome in the specimen collected in step (1) is carried out by using an exosome isolated from the specimen.

[12] The method according to [10] or [11], in which step (2) is carried out by an immunoassay method.

[13] The method according to [12], in which the immunoassay method is carried out by using an antibody binding to GPRC5C or a fragment of the antibody.

[14] The method according to [12], in which the immunoassay method is carried out by using the antibody binding to GPRC5C or a fragment of the antibody and an antibody binding to an exosome-specific antigen or a fragment of the antibody.

[15] The method according to [14], in which the exosome-specific antigen is CD63, CD9, CD81, CD37, CD53, CD82, CD13, CD11, CD86, ICAM-1, Rab5, Annexin V, or LAMP1.

[16] The method according to any one of [9] to [15], in which the pancreatic disease other than pancreatic cancer is pancreatitis.

[17] The method according to any one of [9] to [16], in which the specimen is blood.

[18] A method for monitoring a possibility of a subject having pancreatic cancer, including measuring GPRC5C present in an exosome in a specimen sequentially collected from the subject.

[19] The method according to [18], including the following steps:

(1) a step of sequentially collecting a specimen from a subject;

(2) a step of measuring a concentration of GPRC5C present in an exosome in the specimen collected in step (1); and (3) a step of determining that the possibility of the subject having pancreatic cancer is high in a case where the concentration of GPRC5C measured in step (2) is maintained to be higher than a concentration of GPRC5C present in an exosome in a specimen collected from a healthy person, and determining that the possibility of the subject having pancreatic cancer is low in a case where the concentration measured in step (2) is maintained to be the same as or lower than the concentration of GPRC5C present in the exosome in the specimen collected from the healthy person.

[20] The method according to [19], in which in step (2), measurement of the concentration of GPRC5C present in the exosome in the specimen collected in step (1) is carried out by using an exosome isolated from the specimen.

[21] The method according to [19] or [20], in which step (2) is carried out by using an immunoassay method.

[22] The method according to [21], in which the immunoassay method is carried out by using an antibody binding to GPRC5C or a fragment of the antibody.

[23] The method according to [21], in which the immunoassay method is carried out by using the antibody binding to GPRC5C or a fragment of the antibody and an antibody binding to an exosome-specific antigen or a fragment of the antibody.

[24] The method according to [23], in which the exosome-specific antigen is CD63, CD9, CD81, CD37, CD53, CD82, CD13, CD11, CD86, ICAM-1, Rab5, Annexin V, or LAMP1.

[25] The method according to any one of [18] to [24], in which the specimen is blood.

[26] A reagent for examining a possibility of a subject having pancreatic cancer, including a reagent for measuring GPRC5C present in an exosome in a specimen collected from a subject.

[27] The reagent according to [26], in which the reagent for measuring GPRC5C is an immunoassay reagent.

[28] The reagent according to [27], in which the immunoassay reagent includes an antibody binding to GPRC5C or a fragment of the antibody.

[29] The reagent according to [28], in which the immunoassay reagent further includes an antibody binding to an exosome-specific antigen or a fragment of the antibody.

[30] The reagent according to [29], in which the exosome-specific antigen is CD63, CD9, CD81, CD37, CD53, CD82, CD13, CD11, CD86, ICAM-1, Rab5, Annexin V, or LAMP1.

[31] The reagent according to any one of [26] to [30], further including an exosome isolation reagent.

[32] The reagent according to any one of [26] to [31], in which the specimen is blood.

A reagent for distinguishing a pancreatic cancer patient from a patient having a pancreatic disease other than pancreatic cancer, including a reagent for measuring GPRC5C present in an exosome in a specimen collected from a pancreatic disease patient.

[34] The reagent according to [33], in which the reagent for measuring GPRC5C is an immunoassay reagent.

[35] The reagent according to [34], in which the immunoassay reagent includes an antibody binding to GPRC5C or a fragment of the antibody.

[36] The reagent according to [35], in which the immunoassay reagent further includes an antibody binding to an exosome-specific antigen or a fragment of the antibody.

[37] The reagent according to [36], in which the exosome-specific antigen is CD63, CD9, CD81, CD37, CD53, CD82, CD13, CD11, CD86, ICAM-1, Rab5, Annexin V, or LAMP I.

[38] The reagent according to any one of [33] to [37], further including an exosome isolation reagent.

[39] The reagent according to any one of [33] to [38], in which the pancreatic disease other than pancreatic cancer is pancreatitis.

[40] The reagent according to any one of [33] to [39], in which the specimen is blood.

[41] A reagent for monitoring a possibility of a subject having pancreatic cancer, including a reagent for measuring GPRC5C present in an exosome in a specimen sequentially collected from the subject.

[42] The reagent according to [41], in which the reagent for measuring GPRC5C is an immunoassay reagent.

[43] The reagent according to [42], in which the immunoassay reagent includes an antibody binding to GPRC5C or a fragment of the antibody.

[44] The reagent according to [43], in which the immunoassay reagent further includes an antibody binding to an exosome-specific antigen or a fragment of the antibody.

[45] The reagent according to [44], in which the exosome-specific antigen is CD63, CD9, CD81, CD37, CD53, CD82, CD13, CD11, CD86, ICAM-1, Rab5, Annexin V, or LAMP1.

[46] The reagent according to any one of [41] to [45], further including an exosome isolation reagent.

[47] The reagent according to any one of [41] to [46], in which the specimen is blood.

[48] A pancreatic cancer marker including GPRC5C or a GPRC5C gene.

[49] A pancreatic cancer diagnosis reagent including a specific binding substance to GPRC5C, a primer set capable of amplifying a GPRC5C gene, or a probe specifically hybridized to mRNA of the GPRC5C gene.

[50] The diagnosis reagent according to [49], in which the specific binding substance to GPRC5C is an antibody binding to GPRC5C or a fragment of the antibody.

[51] A method for determining a biological sample, including a step of measuring an amount of GPRC5C in a biological sample and a step of determining that the biological sample is a biological sample of a pancreatic cancer patient in a case where the measured amount of the protein is larger compared to an amount of GPRC5C in a biological sample of a healthy person or a patient having a pancreatic disease other than pancreatic cancer.

[52] A method for determining a biological sample, including a step of measuring an expression amount of a GPRC5C gene in a biological sample and a step of determining that the biological sample is a biological sample of a pancreatic cancer patient in a case where the measured expression amount of the gene is larger compared to an expression amount of a GPRC5C gene in a biological sample of a healthy person or in a biological sample of a patient having a pancreatic disease other than pancreatic cancer.

[53] The method according to [51] or [52], in which the pancreatic disease other than pancreatic cancer is pancreatitis.

Advantageous Effects of Invention

The present invention provides a method and a reagent for examining a possibility of a subject having pancreatic cancer, a method and a reagent for distinguishing pancreatic cancer from a pancreatic disease other than pancreatic cancer, a method and a reagent for monitoring the possibility of the subject having pancreatic cancer, and a pancreatic cancer marker, a pancreatic cancer diagnosis reagent, and a method for determining a biological sample.

MODE FOR CARRYING OUT THE INVENTION

Figure 1:
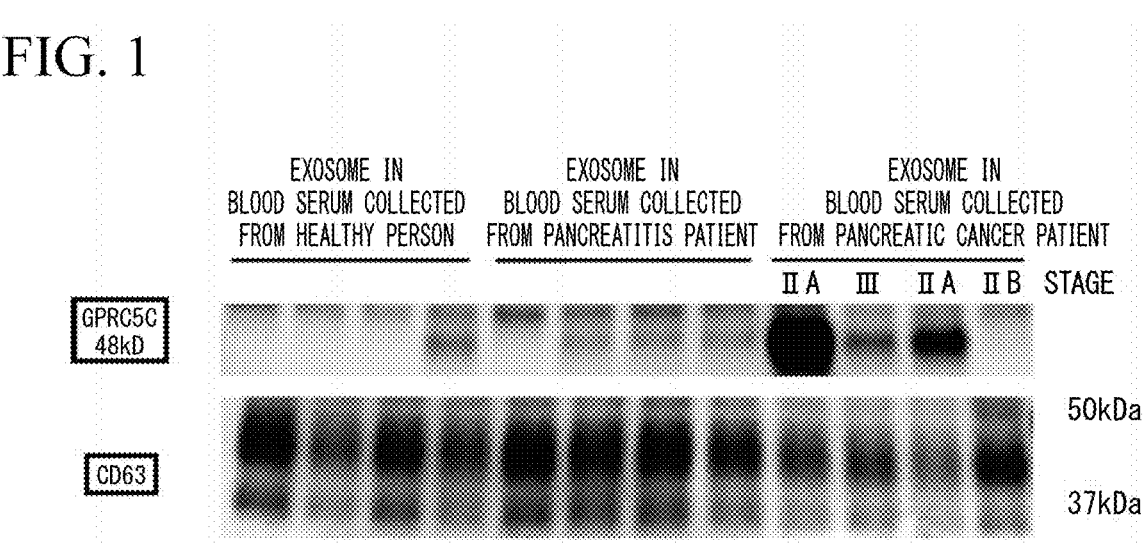
FIG. 1 shows the results of detecting GPRC5C (48 kD) and CD63 which is an exosome-specific antigen by Western blotting by using exosomes in blood serum collected from healthy persons (4 specimens), pancreatitis patients (4 specimens), and pancreatic cancer patients (4 specimens).

1. A Method for Examining a Possibility of a Subject Having Pancreatic Cancer.

A method for examining a possibility of a subject having pancreatic cancer of the present invention is a method of measuring a concentration of GPRC5C present in an exosome in a specimen collected from the subject.

An exosome in the present invention is a membrane vesicle covered with a lipid double membrane having a diameter of 30 to 100 nm secreted from an animal cell.

A specimen in the present invention is not particularly limited as long as it is a specimen capable of measuring GPRC5C present in the exosome, and examples thereof include blood, urine, saliva, milk, nasal mucus, cerebrospinal fluid, and the like, and blood is preferable. Examples of the blood include whole blood, blood serum, plasma, and the like, and blood serum is preferable.

In the present invention, GPRC5C present in the exosome means any forms of GPRC5C such as GPRC5C contained in an exosome, GPRC5C present on a membrane surface of an exosome, and GPRC5C passing through a membrane of an exosome.

In the present invention, the concentration of GPRC5C present in an exosome includes not only an amount or molar amount per unit capacity but also signal intensity per unit capacity.

[Measurement Method 1]

In the present invention, the method for examining a possibility of a subject having pancreatic cancer can be carried out by a method including the following steps.

(1) A step of collecting a specimen from a subject;
(2) A step of measuring a concentration of GPRC5C present in an exosome in the specimen collected step (1);

(3) A step of determining that the possibility of the subject having pancreatic cancer is high in a case where the concentration of GPRC5C measured in step (2) is higher than a concentration of GPRC5C present in an exosome in a specimen collected from a healthy person, and determining that the possibility of the subject having pancreatic cancer is the same as or lower than the concentration of GPRC5C present in the exosome in the specimen collected from the healthy person.

Hereinafter, each step will be described in detail.

<Step (1)>

In step (1), as the specimen collected from the subject, the above-described specimens are exemplified.

<Step (2)>

Step (2) is a step of measuring a concentration of GPRC5C present in an exosome in the specimen collected in step (1). The concentration of GPRC5C present in an exosome in the specimen collected in step (1) can be measured by an immunoassay method, for example. As the immunoassay method, any method can be used as long as the method is a method capable of measuring the concentration of GPRC5C present in an exosome in a specimen using antigen-antibody reaction. For example, a method of using an antibody binding to GPRC5C or a fragment of the antibody, a method of using an antibody binding to GPRC5C or a fragment of the antibody and an antibody binding to an exosome-specific antigen or a fragment of the antibody, and the like can be exemplified.

The antibody binding to GPRC5C in step (2) is not particularly limited as long as it is an antibody capable of measuring GPRC5C, and examples thereof include Anti-GPRC5C antibody-C-terminal (ab137482) (manufactured by Abcam Corporation), GPRC5C Antibody (N-14) (manufactured by Santa Cruz Biotechnology), and the like.

Examples of the exosome-specific antigen in step (2) include CD63, CD9, CD81, CD37, CD53, CD82, CD13, CD11, CD86, ICAM-1, Rab5, Annexin V, LAMP1, and the like.

The antibody binding to the exosome-specific antigen is not particularly limited as long as it is an antibody capable of binding to an exosome-specific antigen. Examples thereof include Purified Mouse Anti-Human CD63 (manufactured by Becton Dickinson Japan, clone: H5C6), Purified Mouse Anti-Human CD9 (manufactured by Becton Dickinson Japan, clone: M-L13), Purified Mouse Anti-Human CD81 (manufactured by Becton Dickinson Japan, clone: JS-81), Purified Mouse Anti-Human CD37 (manufactured by Becton Dickinson Japan, clone: M-B371), Purified Mouse Anti-Human CD53 (manufactured by Becton Dickinson Japan, clone: HI29), Anti-CD82 antibody [C33] (manufactured by Abcam Corporation), Purified Mouse Anti-Human CD13 (manufactured by Becton Dickinson Japan, clone: WM15), Purified Mouse Anti-Human CD11a (manufactured by Becton Dickinson Japan, clone: 27/CD11a), Purified Mouse Anti-Human CD11b/Mac-1 (manufactured by Becton Dickinson Japan, clone: ICRF44), Purified Mouse Anti-Human CD11c (manufactured by Becton Dickinson Japan, clone: 3.9), Purified Mouse Anti-Human CD86 (manufactured by Becton Dickinson Japan, clone: 2331 (FUN-1)), Anti-ICAM1 antibody [HM1] (manufactured by Abcam Corporation), Purified Mouse Anti-Rab5 (manufactured by Becton Dickinson Japan, clone: 1/Rab5), Anti-Annexin V antibody (EPR3979) (manufactured by Abcam Corporation), Purified Mouse Anti-Human Lamp-1 (manufactured by Becton Dickinson Japan, clone: 25/Lamp-1), and the like.

The fragment of the antibody binding to GPRC5C and the fragment of the antibody binding to an exosome-specific antigen in step (2) are not particularly limited as long as the fragment of the antibody binding to GPRC5C and the fragment of the antibody binding to an exosome-specific antigen are fragments of antibodies capable of measuring GPRC5C and an exosome-specific antigen, respectively, and examples thereof include a fragment of an antibody obtained by removing an Fc portion such as Fab obtained by subjecting an antibody to papain treatment, $F(ab')_2$ obtained by pepsin treatment, and Fab' obtained by pepsin treatment-reduction treatment, a fragment of an antibody obtained by removing an Fc portion by gene engineering technique, and the like.

The concentration of GPRC5C present in an exosome in the specimen of step 2 can be measured by sandwich ELISA or ExoScreen method to be described later. In the sandwich ELISA, among the two kinds of antibodies used in measuring the concentration of GPRC5C present in the exosome, the antibody binding to an exosome-specific antigen or a fragment of the antibody can be used as a solid-phase antibody, and the antibody binding to GPRC5C or a fragment of the antibody can be used as a labeled antibody. Or, the antibody binding to GPRC5C or a fragment of the antibody can be used as a solid-phase antibody, and the antibody binding to an exosome-specific antigen or a fragment of the antibody can be used as a labeled antibody. Preparation of the solid-phase antibody and the labeled antibody is not particularly limited, and can be carried out by a known method.

The measurement method of GPRC5C present in an exosome can be carried out by using any method as long as the method is capable of measuring GPRC5C present in an exosome. For example, a method such as an immunoassay method can be used.

Specifically, in a case where an antibody binding to GPRC5C or a fragment of the antibody is used as a solid-phase antibody, and an antibody binding to an exosome-specific antigen or a fragment of the antibody is used as a labeled antibody, an exosome including GPRC5C in a specimen binds to GPRC5C immobilized to a solid phase, subsequently, a labeled antibody binding to an exosome-specific antigen or a fragment of the antibody is added thereto, a complex of the antibody binding to GPRC5C or a fragment of the antibody, an exosome, and a labeled antibody binding to an exosome-specific antigen or a fragment of the antibody is formed in a solid phase, the label in the formed complex is measured, and thereby GPRC5C present in the exosome can be measured.

In addition, in a case where an antibody binding to an exosome-specific antigen or a fragment of the antibody is used as a solid-phase antibody, and an antibody binding to GPRC5C or a fragment of the antibody is used as a labeled antibody, the exosome in the specimen binds to an antibody binding to an exosome-specific antigen or a fragment of the antibody immobilized to a solid phase, subsequently, a labeled antibody binding to GPRC5C or a fragment of the antibody is added thereto, a complex of the antibody binding to an exosome-specific antigen or a fragment of the antibody, an exosome, and a labeled antibody binding to GPRC5C or a fragment of the antibody is formed in a solid phase, and the label in the formed complex is measured, and thereby GPRC5C present in the exosome can be measured.

In the above description, as the solid phase, for example, various membranes such as microtiter plate, granular substances (beads) made of glass or synthetic resin, spherical substances (balls) made of glass or synthetic resin, latex, magnetic particles, nitrocellulose membrane, a test tube made of synthetic resin, and the like can be used. As the label, for example, an enzyme, a fluorescent substance, a light emission substance, a radioactive isotope, biotin, digoxigenin, polypeptide including a tag sequence, metal colloid particles, colored latex particles, and the like can be used.

As the enzyme, for example, alkali phosphatase, peroxidase, galactosidase, glucuronidase, luciferase, and the like can be exemplified.

As the fluorescent substance, for example, fluorescein isothiocyanate (FITC), rhodamine B isothiocyanate (RITC), and the like can be exemplified. As other fluorescent substances, for example, quantum dot (Science, 281, 2016-2018, 1998), a phycobiliprotein such as phycoerythrin, and proteins emitting fluorescence such as GFP (Green fluorescent Protein), RFP (Redfluorescent Protein), YFP (Yellow fluorescent Protein), and BFP (Blue fluorescent Protein) are exemplified.

As the light emission substance, for example, acridinium and the derivative, a ruthenium complex compound, lophine, and the like are exemplified. As the ruthenium complex compound, those shown in Clin. Chem. 37, 9, 1534-1539, 1991, which electrochemically emit light along with an electron donor, are preferable.

As the radioactive isotope, for example, $^3H$, $^{14}C$, $^{35}S$, $^{32}P$, $^{125}I$, $^{131}I$, and the like are exemplified.

As the polypeptide including a tag sequence, FLAG peptide (FLAG tag, Asp Tyr Lys Asp Asp Asp Asp Lys), polyhistidine (His tag, His His His His His His), myc epitope peptide (myc tag, Glu Gln Lys Leu Ile Ser Glu Glu Asp Leu), hemagglutinin epitope peptide (HA tag, Tyr Pro Tyr Asp Val Pro Asp Tyr Ala), and the like are exemplified.

In step (2), in a case of measuring the concentration of GPRC5C present in the exosome in the specimen without disrupting the exosome in the specimen, as the antibody binding to GPRC5C or a fragment of the antibody, among the antibody binding to GPRC5C or a fragment of the antibody, an antibody binding to an epitope of GPRC5C present on an exosome surface or a fragment of the antibody is preferably used.

As the immunoassay method in step (2), in addition to the above-described sandwich ELISA, an ExoScreen method is exemplified. The ExoScreen method is a method applying AlphaLISA developed by PerkinElmer Corporation. In this method, using two kinds of antibodies of which epitopes are different, as one antibody, a biotinized antibody bonded to biotin, and as the other antibody, an antibody bonded to AlphaLISA acceptor bead are used to perform reaction with an analysis sample. After that, by adding a donor bead bonded to streptoavidine, the biotinized antibody and the donor bead bind to each other via streptoavidin, and the acceptor bead and the donor bead are adjacent to each other. In a state of being adjacent within a range of 200 nm, by 680 nm excitation, a singlet enzyme is generated from the donor bead, and when the singlet enzyme reaches the acceptor bead, light of 615 nm is emitted and can be detected as a signal.

Specifically, the biotinized antibody in which the antibody binding to GPRC5C or a fragment of the antibody is bonded to biotin, and the antibody binding to an exosome-specific antigen or a fragment of the antibody bonded to AlphaLISA acceptor bead are reacted with GPRC5C present in the exosome in the specimen, and thereafter, by adding a donor bead bonded to streptoavidin, a complex of the acceptor bead, the exosome, and the donor bead is formed. Excitation light is irradiated on the donor bead of the complex to generate a singlet enzyme, and light generated by reaction of the generated singlet enzyme and the acceptor bead is measured.

In addition, the biotinized antibody in which the antibody binding to an exosome-specific antigen or a fragment of the antibody is bonded to biotin, and the antibody binding to GPRC5C bonded to AlphaLISA acceptor bead or a fragment of the antibody are reacted with GPRC5C present in the exosome in the specimen, and thereafter, by adding a donor bead bonded to streptoavidin, a complex of the acceptor bead, the exosome, and the donor bead is formed. Excitation light is irradiated on the donor bead of the complex to generate a singlet enzyme, and light generated by reaction of the generated singlet enzyme and the acceptor bead is measured.

<Step (3)>

Step (3) is a step of comparing a concentration of GPRC5C present in the exosome in the specimen collected from the subject, obtained in step (2), with a concentration of GPRC5C present in an exosome in a specimen collected from a healthy person. In a case where the concentration of GPRC5C present in the exosome in the specimen collected from the subject is higher than the concentration of GPRC5C present in the exosome in the specimen collected from the healthy person, it is determined that the possibility of the subject having pancreatic cancer is high, and in a case where the concentration of GPRC5C present in the exosome in the specimen collected from the subject is the same as or lower than the concentration of GPRC5C present in the exosome in the specimen collected from the healthy person, it is determined that the possibility of the subject having pancreatic cancer is low.

The concentration of GPRC5C present in the exosome in the specimen collected from the healthy person is a criteria value for determining the possibility of the subject having pancreatic cancer, and the concentration of GPRC5C present in the exosome in the specimen collected from the healthy person can be set by measuring concentrations of GPRC5C present in the exosome in the specimens collected from a plurality of healthy persons, and statistically analyzing.

As the specimen collected from the healthy person, the same kind of sample as that of the specimen collected from the subject is preferable. For example, in a case where the specimen collected from the subject is blood, as the specimen collected from the healthy person, blood is also preferably used.

The method of comparing the concentration of GPRC5C present in the exosome in the specimen collected from the subject with the concentration of GPRC5C present in the exosome in the specimen collected from the healthy person is not particularly limited, and a known method (Steel method, t test, Wilcoxon test, and the like) can be used. From the comparison, in a case where the concentration of GPRC5C present in the exosome in the specimen collected from the subject is higher than the concentration of GPRC5C present in the exosome in the specimen collected from the healthy person, it is determined that the possibility of the subject having pancreatic cancer is high, and in a case where the concentration of GPRC5C present in the exosome in the specimen collected from the subject is the same as or lower than the concentration of GPRC5C present in the exosome in the specimen collected from the healthy person, it is determined that the possibility of the subject having pancreatic cancer is low.

In addition, as a criteria value for determining the possibility of the subject having pancreatic cancer, instead of the concentration of GPRC5C present in the exosome in the specimen collected from the healthy person, a ratio of the concentration of GRPC5C present in the exosome in the specimen collected from the healthy person with respect to the concentration of the exosome-specific antigen can be used. In this case, a ratio of the concentration of GPRC5C present in the exosome in the specimen collected from the subject with respect to the concentration of the exosome-specific antigen is compared with a ratio of the concentration of GPRC5C present in the exosome in the specimen collected from the healthy person with respect to the concentration of the exosome-specific antigen. As the exosome-specific antigen, for example, the above-described exosome-specific antigen and the like are exemplified.

In addition, in step (2) of measurement method 1, the concentration of GPRC5C present in the exosome in the specimen can be measured by using an exosome isolated from the specimen collected from the subject. Specifically, a method including the following steps is exemplified.

[Measurement Method 2]

(1A) A step of collecting a specimen from a subject;

(2A) A step of isolating an exosome from the specimen collected in step (1A);

(3A) A step of measuring a concentration of GPRC5C present in the exosome isolated in step (2A);

(4A) A step of determining a concentration of GPRC5C present in an exosome in the specimen from the concentration of GPRC5C measured in step (3A);

(5A) A step of determining that the possibility of the subject having pancreatic cancer is high in a case where the concentration of GPRC5C determined in step (4A) is higher than a concentration of GPRC5C present in an exosome in a specimen collected from a healthy person, and determining that the possibility of the subject having pancreatic cancer is low in a case where the concentration of GPRC5C determined in step (4A) is the same as or lower than the concentration of GPRC5C present in the exosome in the specimen collected from the healthy person.

Hereinafter, each step will be described in detail.

<Step (1A)>

In step (1A), as the specimen collected from the subject, the above-described specimen and the like are exemplified.

<Step (2A)>

In step (2A), the method of isolating the exosome is not particularly limited as long as it is a method capable of isolating the exosome in the specimen. For example, an ultracentrifugation method (Trends in Molecular Medicine. 21, 533 (2015)), a method of using exosome isolation kit EXO-Prep (manufactured by Cosmo Bio Co., Ltd), and the like are exemplified.

<Step (3A)>

As the measurement method of the concentration of GPRC5C present in the exosome in step (3A), any method can be used as long as it is capable of measuring the concentration of GPRC5C present in the exosome. For example, a method such as an immunoassay method can be used. As the measurement method of the concentration of GPRC5C present in the exosome by an immunoassay method, the following aspects are exemplified.

Aspect 1

A method of using an antibody binding to GPRC5C or a fragment of the antibody.

Aspect 2

A method of using an antibody binding to GPRC5C or a fragment of the antibody and an antibody binding to an exosome-specific antigen or a fragment of the antibody.

As the antibody binding to GPRC5C or a fragment of the antibody, for example, the above-described antibody binding to GPRC5C or a fragment of the antibody and the like are exemplified. As the antibody binding to an exosome-specific antigen or a fragment of the antibody, for example, the above-described antibody binding to an exosome-specific antigen or a fragment of the antibody and the like are exemplified.

As the method of Aspect 1, for example, Western blotting and the like are exemplified. As the Western blotting, for example, the method described in Monoclonal Antibodies-Principles and practices, Third edition, Academic Press (1996) and the like are exemplified.

As the method of Aspect 2, in a case of measurement without disrupting an isolated exosome, the immunoassay method described in measurement method 1, for example, the ExoScreen method is exemplified. In addition, in a case of measurement by disrupting an isolated exosome, the sandwich ELISA method and the like are exemplified. As the ExoScreen method, for example, the above-described ExoScreen method and the like are exemplified.

In a case of measurement without disrupting an isolated exosome, as the antibody binding to GPRC5C or a fragment of the antibody, among the antibody binding to GPRC5C or a fragment of the antibody, an antibody binding to an epitope of GPRC5C present on an exosome surface or a fragment of the antibody is used.

As the method of disrupting an isolated exosome, for example, a method of using ultrasonic waves and the like are exemplified. As the sandwich ELISA method, for example, the antibody binding to GPRC5C or a fragment of the antibody can be used as a solid-phase antibody, and the antibody binding to an exosome-specific antigen or a fragment of the antibody may be used as a labeled antibody, or the antibody binding to an exosome-specific antigen or a fragment of the antibody may be used as a solid-phase antibody, and the antibody binding to GPRC5C or a fragment of the antibody can be used as a labeled antibody. As the solid phase and the label, for example, known solid phase and label are respectively exemplified, and for example, the above-described solid phase and the above-described label are respectively used. As a method of preparing the solid phase-antibody and the labeled antibody, for example, a known preparation method is exemplified.

<Step (4A)>

Step (4A) is a step of determining a concentration of GPRC5C present in an exosome in the specimen from the concentration of GPRC5C measured in step (3A). A concentration of GPRC5C present in an exosome in the specimen can be determined from the capacity of the specimen and the concentration of GPRC5C measured in step (3A).

<Step (5A)>

Step (5A) is a step of comparing the concentration of GPRC5C present in an exosome in the specimen collected from the subject, determined in step (4A), with a concentration of GPRC5C present in an exosome in a specimen collected from a healthy person. In a case where the concentration of GPRC5C present in the exosome in the specimen collected from the subject is higher than the concentration of GPRC5C present in the exosome in the specimen collected from the healthy person, it is determined that the possibility of the subject having pancreatic cancer is high, and in a case where the concentration of GPRC5C present in the exosome in the specimen collected from the subject is the same as or lower than the concentration of GPRC5C present in the exosome in the specimen collected from the healthy person, it is determined that the possibility of the subject having pancreatic cancer is low.

The concentration of GPRC5C present in the exosome in the specimen collected from the healthy person is a criteria value for determining the possibility of the subject having pancreatic cancer, and the concentration of GPRC5C present in an exosome in the specimen collected from the healthy person can be set by measuring concentrations of GPRC5C present in the exosome in the specimen collected from a plurality of healthy persons, and statistically analyzing.

As the specimen of the healthy person, the same kind of sample as that of the specimen of the subject is preferable. For example, in a case where the specimen of the subject is blood, as the specimen of the healthy person, blood is preferably used.

As the method of comparing the concentration of GPRC5C present in the exosome in the specimen collected from the subject with the concentration of PGRC5C present in the exosome in the specimen collected from the healthy person, the above-described method can be used. From the comparison, in a case where the concentration of GPRC5C present in the exosome in the specimen collected from the subject is shown to be higher than the concentration of GPRC5C present in the specimen collected from the healthy person, it is determined that the possibility of the subject having pancreatic cancer is high, and in a case where the concentration of GPRC5C present in the exosome in the specimen collected from the subject is shown to be the same as or lower than the concentration of GPRC5C present in the exosome in the specimen collected from the healthy person, it is determined that the possibility of the subject having pancreatic cancer is low.

In addition, as a criteria value for determining the possibility of the subject having pancreatic cancer, instead of the concentration of GPRC5C present in the exosome in the specimen collected from the healthy person, a ratio of the concentration of GPRC5C present in the exosome in the specimen collected from the healthy person with respect to the concentration of the exosome-specific antigen can be used. In this case, a ratio of the concentration of GPRC5C present in the exosome in the specimen collected from the subject with respect to the concentration of the exosome-specific antigen is compared with a ratio of the concentration of GPRC5C present in the exosome in the specimen collected from the healthy person with respect to the concentration of the exosome-specific antigen. As the exosome-specific antigen, for example, the above-described exosome-specific antigen and the like are exemplified.

2. A method of distinguishing pancreatic cancer from a pancreatic disease other than pancreatic cancer in a pancreatic disease patient The method of distinguishing pancreatic cancer from a pancreatic disease other than pancreatic cancer in a pancreatic disease patient of the present invention is a method of measuring a concentration of GPRC5C present in an exosome in a specimen collected from a pancreatic disease patient.

The specimen in the distinguishing method of the present invention is not particularly limited as long as it is a specimen from which GPRC5C present in the exosome can be measured. For example, the above-described specimen and the like are exemplified.

In the distinguishing method of the present invention, GPRC5C present in the exosome may be present in any forms, for example, may be contained in the exosome, may be present on a membrane surface of the exosome, or may pass through a membrane of the exosome.

In the distinguishing method of the present invention, the concentration of GPRC5C present in the exosome includes not only a mass or a molar amount per unit capacity but also signal intensity per unit capacity.

[Measurement Method 3]

In the pancreatic disease patient of the present invention, the method of distinguishing pancreatic cancer from a pancreatic disease other than pancreatic cancer can be carried out by a method including the following steps.

(1B) A step of collecting a specimen from a subject;

(2B) A step of measuring a concentration of GPRC5C present in an exosome in the specimen collected in step (1B);

(3B) A step of determining that the possibility of the subject having pancreatic cancer is high in a case where the concentration of GPRC5C present in the exosome measured in step (2B) is higher than a concentration of GPRC5C present in an exosome in a specimen collected from a patient having a pancreatic disease other than pancreatic cancer, and determining that the possibility of the subject having pancreatic cancer is low in a case where the concentration of GPRC5C present in the exosome measured in step (2B) is the same as or lower than the concentration of GPRC5C present in the exosome in the specimen collected from the patient having a pancreatic disease other than pancreatic cancer.

Hereinafter, each step will be described in detail.

<Step (1B)>

In step (1B), as the specimen collected from the subject, the above-described specimen and the like are exemplified.

<Step (2B)>

As the measurement method of the concentration of GPRC5C present in the exosome in step (2B), any method can be used as long as the method is a method capable of measuring the concentration of GPRC5C present in the exosome. For example, a method such as an immunoassay method can be used. As the measurement method of the concentration of GPRC5C present in the exosome by the immunoassay method, the following aspects are exemplified.

Aspect 1

A method of using an antibody binding to GPRC5C or a fragment of the antibody.

Aspect 2

A method of using an antibody binding to GPRC5C or a fragment of the antibody and an antibody binding to an exosome-specific antigen or a fragment of the antibody.

The antibody binding to GPRC5C or a fragment of the antibody in step (2B) is not particularly limited as long as the antibody binding to GPRC5C or a fragment of the antibody is an antibody capable of measuring GPRC5C or a fragment of the antibody. For example, the above-described antibody or a fragment of the antibody and the like are exemplified.

As the exosome-specific antigen in step (2B), for example, the above-described antigen and the like are exemplified.

The antibody binding to the exosome-specific antigen or a fragment of the antibody in step (2B) is not particularly limited as long as the antibody binding to the exosome-specific antigen or a fragment of the antibody is an antibody capable of binding to an exosome-specific antigen or a fragment of the antibody. For example, the above-described antibody or a fragment of the antibody and the like are exemplified.

In step (2B), in a case of using the two kinds of antibodies or a fragment of the antibody, the concentration of GPRC5C present in the exosome can be measured by using the antibody binding to an exosome-specific antigen or a fragment of the antibody as a solid-phase antibody and using the antibody binding to GPRC5C or a fragment of the antibody as a labeled antibody. In addition, the concentration of GPRC5C present in the exosome can be measured by using the antibody binding to GPRC5C or a fragment of the antibody as a solid-phase antibody and using the antibody binding to an exosome-specific antigen or a fragment of the antibody as a labeled antibody. Preparation of the solid-phase antibody and the labeled antibody is not particularly limited, and can be carried out by a known method.

As the measurement method of GPRC5C present in the exosome, any method can be used as long as it is capable of measuring GPRC5C present in the exosome. For example, an immunoassay method such as the above-described sandwich ELISA and the ExoScreen method can be used.

In step (2B), in a case of measuring the concentration of GPRC5C present in the exosome in the specimen without disrupting the exosome in the specimen, as an antibody binding to GPRC5C or a fragment of the antibody, among the above-described antibody binding to GPRC5C or a fragment of the antibody, an antibody binding to an epitope of GPRC5C present on an exosome surface or a fragment of the antibody is preferably used.

<Step (3B)>

Step (3B) is a step of comparing the concentration of GPRC5C present in the exosome in the specimen collected from the pancreatic disease patient, obtained in step (2B), with the concentration of GPRC5C present in the exosome in the specimen collected from the patient having a pancreatic disease other than pancreatic cancer, and is a step of determining that the possibility of the pancreatic disease patient having pancreatic cancer is high in a case where the concentration of GPRC5C present in the exosome in the specimen collected from the pancreatic disease patient is higher than the concentration of GPRC5C in the specimen collected from the patient having a pancreatic disease other than pancreatic cancer, and determining that the possibility of the pancreatic disease patient having a pancreatic disease other than pancreatic cancer is high in a case where the concentration of GPRC5C present in the exosome in the specimen collected from the pancreatic disease patient is the same as or lower than the concentration of GPRC5C in the specimen collected from the patient having a pancreatic disease other than pancreatic cancer.

As the pancreatic disease other than pancreatic cancer, pancreatitis is exemplified. As the pancreatitis, chronic pancreatitis and acute pancreatitis are exemplified.

The concentration of GPRC5C present in the exosome in the specimen collected from the patient having a pancreatic disease other than pancreatic cancer is a criteria value for distinguishing whether the subject has pancreatic cancer or has a pancreatic disease other than pancreatic cancer, and the concentration of GPRC5C present in an exosome in the specimen collected from a patient having a pancreatic disease other than pancreatic cancer can be set by measuring concentrations of GPRC5C present in the exosome in the specimen collected from a plurality of patients having a pancreatic disease other than pancreatic cancer and statistically analyzing.

As the specimen collected from the patient having a pancreatic disease other than pancreatic cancer, the same kind of sample as that of the specimen collected from the subject is preferable. For example, in a case where the specimen collected from the subject is blood, as the specimen collected from the patient having a pancreatic disease other than pancreatic cancer, blood is also preferably used.

The method of comparing the concentration of GPRC5C present in the exosome in the specimen collected from the subject with the concentration of GPRC5C present in the exosome in the specimen collected from the patient having a pancreatic disease other than pancreatic cancer is not particularly limited. For example, the above-described method can be used. From the comparison, in a case where the concentration of GPRC5C present in the exosome in the specimen collected from the subject is higher than the concentration of GPRC5C present in the exosome in the specimen collected from the patient having a pancreatic disease other than pancreatic cancer, it is determined that the possibility of the subject having pancreatic cancer is high, and in a case where the concentration of GPRC5C present in the exosome in the specimen collected from the subject is the same as or lower than the concentration of GPRC5C present in the exosome in the specimen collected from the patient having a pancreatic disease other than pancreatic cancer, it is determined that the possibility of the subject having a pancreatic disease other than pancreatic cancer is high.

In addition, in the pancreatic disease patient, as a criteria value for distinguishing pancreatic cancer from a pancreatic disease patient, instead of the concentration of GPRC5C present in the exosome in the specimen collected from a patient having pancreatic disease other than pancreatic cancer, a ratio of the concentration of GPRC5C present in the exosome in the specimen collected from the patient having pancreatic disease other than pancreatic cancer with respect to the exosome-specific antigen can be used. In this case, a ratio of the concentration of GPRC5C present in the exosome in the specimen collected from the pancreatic disease patient with respect to the concentration of the exosome-specific antigen is compared with a ratio of the concentration of GPRC5C present in the exosome in the specimen collected from the patient having pancreatic disease other than pancreatic cancer with respect to the concentration of the exosome-specific antigen. As the exosome-specific antigen, for example, the above-described exosome-specific antigen and the like are exemplified.

In addition, in step (2B) of measurement method 3, the concentration of GPRC5C present in the exosome in the specimen can be measured by using an exosome isolated from the specimen collected from the subject. Specifically, a method including the following steps is exemplified.

[Measurement Method 4]

(1C) A step of collecting a specimen from a pancreatic disease patient;

(2C) A step of isolating an exosome from the specimen collected in step (1C);

(3C) A step of measuring a concentration of GPRC5C present in the exosome isolated in step (2C);

(4C) A step of determining a concentration of GPRC5C present in an exosome in the specimen from the concentration of GPRC5C measured in step (3C);

(5C) A step of determining that the possibility of the subject having pancreatic cancer is high in a case where the concentration of GPRC5C determined in step (4C) is higher than a concentration of GPRC5C present in an exosome in a specimen collected from a patient having a pancreatic disease other than pancreatic cancer, and determining that the possibility of the subject having a pancreatic disease other than cancer is high in a case where the concentration of GPRC5C determined in step (4C) is the same as or lower than the concentration of GPRC5C present in the exosome in the specimen collected from the patient having a pancreatic disease other than pancreatic cancer.

<Step (1C)>

In step (1C), as the specimen collected from the subject, the above-described specimen and the like are exemplified.

<Step (2C)>

In step (2C), the method of isolating an exosome is not particularly limited as long as it is a method capable of isolating an exosome in a specimen. For example, the above-described method and the like are exemplified.

<Step (3C)>

As the measurement method of the concentration of GPRC5C present in the exosome in step (3C), any method can be used as long as it is capable of measuring a concentration of GPRC5C present in an exosome. For example, a method such as an immunoassay method can be used. As the measurement method of the concentration of GPRC5C present in the exosome by the immunoassay method, the following aspects are exemplified.

Aspect 1

A method of using an antibody binding to GPRC5C or a fragment of the antibody.

Aspect 2

A method of using an antibody binding to GPRC5C or a fragment of the antibody and an antibody binding to an exosome-specific antigen or a fragment of the antibody.

As the antibody binding to GPRC5C or a fragment of the antibody, for example, the above-described antibody binding to GPRC5C or a fragment of the antibody and the like are exemplified. As the antibody binding to an exosome-specific antigen or a fragment of the antibody, for example, the above-described antibody binding to an exosome-specific antigen or a fragment of the antibody and the like are exemplified.

As the method of Aspect 1, for example Western blotting and the like are exemplified. As the Western blotting, for example, the above-described method and the like are exemplified.

As the method of Aspect 2, in a case of measuring without disrupting the isolated exosome, the immunoassay method described in measurement method 1, for example, the ExoScreen method and the like are exemplified, and in a case of measuring by disrupting the isolated exosome, the sandwich ELISA and the like are exemplified. As the ExoScreen method, for example, the above-described ExoScreen method and the like are exemplified.

In a case of measuring without disrupting the isolated exosome, as an antibody binding to GPRC5C or a fragment of the antibody, among the above-described antibody binding to GPRC5C or a fragment of the antibody, an antibody binding to an epitope of GPRC5C present on an exosome surface or a fragment of the antibody is used.

As the method of disrupting the isolated exosome, for example, the above-described method and the like are exemplified.

As the sandwich ELISA method, for example, the antibody binding to GPRC5C or a fragment of the antibody may be used as a solid-phase antibody and the antibody binding to an exosome-specific antigen or a fragment of the antibody may be used as a labeled antibody, and the antibody binding to an exosome-specific antigen or a fragment of the antibody may be used as a solid-phase antibody and the antibody binding to GPRC5C or a fragment of the antibody may be used as a labeled antibody. As the solid phase or the label, for example, known solid phase and label are respectively exemplified. For example, the above-described solid phase and the label are respectively used. As a method of preparing the solid-phase antibody and the labeled antibody, for example, a known preparation method is exemplified.

<Step (4C)>

Step (4C) is a step of determining a concentration of GPRC5C present in an exosome in the specimen from the concentration of GPRC5C measured in step (3C). A concentration of GPRC5C present in an exosome of the specimen can be determined from the capacity of the specimen and the concentration of GPRC5C measured in step (3C).

<Step (5C)>

Step (5C) is a step of comparing a concentration of GPRC5C present in the exosome in the specimen collected from the pancreatic disease patient, determined in step (4C), with a concentration of GPRC5C present in an exosome in a specimen collected from a patient having a pancreatic disease other than pancreatic cancer. In a case where the concentration of GPRC5C present in the exosome in the specimen collected from the pancreatic disease patient is higher than the concentration of GPRC5C present in the exosome in the specimen collected from a patient having the pancreatic disease other than pancreatic cancer, it is determined that the possibility of the pancreatic disease patient having pancreatic cancer is high, and in a case where the concentration of GPRC5C present in the exosome in the specimen collected from a patient having the pancreatic disease is the same as or lower than the concentration of GPRC5C present in the exosome in the specimen collected from a patient having the pancreatic disease other than pancreatic cancer, it is determined that the possibility of the pancreatic disease patient having a pancreatic disease other than pancreatic cancer is high.

The concentration of GPRC5C present in the exosome in the specimen collected from the patient having a pancreatic disease other than pancreatic cancer is a criteria value for distinguishing whether the pancreatic disease patient has pancreatic cancer or has a pancreatic disease other than pancreatic cancer, and the concentration of GPRC5C present in the exosome in the specimen collected from the patient having a pancreatic disease other than pancreatic cancer can be set by measuring concentrations of GPRC5C present in the exosome in the specimens collected from a plurality of patients having a pancreatic disease other than pancreatic cancer and statistically analyzing. In this case, the specimen of the patient having a pancreatic disease other than pancreatic cancer used at a time of setting the criteria value is preferably the same kind of sample as that of the specimen of the pancreatic disease patient which is a subject. For example, in a case where the specimen of the pancreatic disease patient which is a subject is blood, as the specimen of the patient having a pancreatic disease other than pancreatic cancer, blood is also preferably used.

As a method of comparing the concentration of GPRC5C present in the exosome of the subject with the concentration of GPRC5C present in the exosome of the patient having a pancreatic disease other than pancreatic cancer, the above-described method can be used. From the comparison, in a case where the concentration of GPRC5C present in the exosome in the specimen collected from the subject is shown to be higher than the concentration of GPRC5C present in the exosome in the specimen collected from the patient having a pancreatic disease other than pancreatic cancer, it is determined that the possibility of the subject having pancreatic cancer is high, and in a case where the concentration of GPRC5C present in the exosome in the specimen collected from the subject is shown to be the same as or lower than the concentration of GPRC5C present in the exosome in the specimen collected from a pancreatic disease other than pancreatic cancer, it is determined that the possibility of the subject having a pancreatic disease other than pancreatic cancer is high.

In addition, in the pancreatic disease patient, as a criteria value for distinguishing pancreatic cancer from a patient having a pancreatic disease other than pancreatic cancer, instead of the concentration of GPRC5C present in the exosome in the specimen collected from a patient having pancreatic disease other than pancreatic cancer, a ratio of the concentration of GPRC5C present in the exosome in the specimen collected from the patient having pancreatic disease other than pancreatic cancer with respect to the concentration of the exosome-specific antigen can be used. In this case, a ratio of the concentration of GPRC5C present in the exosome in the specimen collected from the pancreatic disease patient with respect to the concentration of the exosome-specific antigen is compared with a ratio of the concentration of GPRC5C present in the exosome in the specimen collected from the patient having pancreatic disease other than pancreatic cancer with respect to the concentration of the exosome-specific antigen. As the exosome-specific antigen, for example, the above-described exosome-specific antigen and the like are exemplified.

3. A Method of Monitoring a Possibility of a Subject Having Pancreatic Cancer

The method of monitoring a possibility of a subject having pancreatic cancer of the present invention is a method of measuring a concentration of GPRC5C present in an exosome in a specimen sequentially collected from the subject.

The specimen in the present invention is not particularly limited as long as it is capable of measuring GPRC5C present in an exosome. For example, the above-described specimen and the like are exemplified.

In the present invention, GPRC5C present in the exosome may be present in any forms, for example, may be contained in an exosome, may be present on a membrane surface of an exosome, or may pass through a membrane of an exosome.

In the present invention, the concentration of GPRC5C present in an exosome includes not only an amount or molar amount per unit capacity but also signal intensity per unit capacity.

[Measurement Method 5]

In the present invention, the method of monitoring a possibility of a subject having pancreatic cancer can be carried out by a method including the following steps.

(1D) A step of sequentially collecting a specimen from a subject;

(2D) A step of measuring a concentration of GPRC5C present in an exosome in the specimen collected in step (1D);

(3D) A step of determining that the possibility of the subject having pancreatic cancer is high in a case where the concentration of GPRC5C measured in step (2D) is maintained at a concentration higher than a concentration of GPRC5C present in an exosome in a specimen collected from a healthy person, and determining that the possibility of the subject having pancreatic cancer is low in a case where the concentration of GPRC5C measured in step (2D) is maintained at a concentration the same as or lower than the concentration of GPRC5C present in the exosome in the specimen collected from the healthy person.

<Step (1D)>

In step (1D), as the specimen collected from the subject, the above-described specimen and the like are exemplified.

<Step (2D)>

As the method of measuring the concentration of GPRC5C present in an exosome in step (2D), any method can be used as long as it is a method capable of measuring a concentration of GPRC5C present in an exosome. For example, a method such as an immunoassay method can be used. As the measurement method of the concentration of GPRC5C present in an exosome by an immunoassay method, the following aspects are exemplified.

Aspect 1

A method of using an antibody binding to GPRC5C or a fragment of the antibody.

Aspect 2

A method of using an antibody binding to GPRC5C or a fragment of the antibody and an antibody binding to an exosome-specific antigen or a fragment of the antibody.

The antibody binding to GPRC5C or a fragment of the antibody in step (2D) is not particularly limited as long as it is an antibody capable of measuring GPRC5C or a fragment of the antibody. For example, the above-described antibody or a fragment of the antibody and the like are exemplified.

As the exosome-specific antigen in step (2D), for example, the above-described antigen and the like are exemplified.

The antibody binding to an exosome-specific antigen or a fragment of the antibody in step (2D) is not particularly limited as long as it is an antibody capable of binding to an exosome-specific antigen or a fragment of the antibody. For example, the above-described antibody or a fragment of the antibody and the like are exemplified. In step (2D), in a case of using the two kinds of antibodies or a fragment of the antibody, the concentration of GPRC5C present in an exosome can be measured by using the antibody binding to an exosome-specific antigen or a fragment of the antibody as a solid-phase antibody and using the antibody binding to GPRC5C or a fragment of the antibody as a labeled antibody. In addition, the concentration of GPRC5C present in an exosome can be measured by using the antibody binding to GPRC5C or a fragment of the antibody as a solid-phase antibody and using the antibody binding to an exosome-specific antigen or a fragment of the antibody as a labeled antibody. Preparation of the solid-phase antibody and the labeled antibody is not particularly limited, and can be carried out by a known method.

The measurement method of GPRC5C present in an exosome can be carried out by using any method as long as it is capable of measuring GPRC5C present in an exosome. For example, an immunoassay method such as the above-described sandwich ELISA and ExoScreen method and the like can be used.

In step (2D), in a case of measuring the concentration of GPRC5C present in the exosome in the specimen without disrupting the exosome in the specimen, as the antibody binding to GPRC5C or a fragment of the antibody, among the above-described antibody binding to GPRC5C or a fragment of the antibody, an antibody binding to an epitope of GPRC5C present on an exosome surface or a fragment of the antibody is preferably used.

<Step (3D)>

Step (3D) is a method of comparing the concentration of GPRC5C present in the exosome in the specimen collected from the subject, obtained in step (2D), with the concentration of GPRC5C present in the exosome in the specimen collected from a healthy person. It is determined that the possibility of the subject having pancreatic cancer is high in a case where the concentration of GPRC5C present in the exosome in the specimen collected from the subject is higher than a concentration of GPRC5C present in an exosome in a specimen collected from a healthy person, and it is determined that the possibility of the subject having pancreatic cancer is low in a case where the concentration of GPRC5C present in the exosome in the specimen collected from the subject is the same as or lower than the concentration of GPRC5C present in the exosome in the specimen collected from the healthy person.

The concentration of GPRC5C present in the exosome in the specimen collected from the healthy person is a criteria value for determining the possibility of the subject having pancreatic cancer, and the concentration of GPRC5C present in an exosome in a specimen collected from the healthy person can be set by measuring concentrations of GPRC5C present in the exosome in the specimens collected from a plurality of healthy persons and statistically analyzing.

As the specimen collected from the healthy person, the same kind of sample as that of the specimen collected from the subject is preferable. For example, in a case where the specimen collected from the subject is blood, as the specimen collected from the healthy person, blood is also preferably used.

The method of comparing the concentration of GPRC5C present in the exosome in the specimen sequentially collected from the subject with the concentration of GPRC5C present in the exosome in the specimen collected from the healthy person is not particularly limited. For example, the above-described method and the like can be used. From the comparison, in a case where the concentration of GPRC5C present in the exosome in the specimen collected from the subject is maintained at a concentration higher than the concentration of GPRC5C present in the exosome in the specimen collected from the healthy person, it is determined that the possibility of the subject having pancreatic cancer is high, and in a case where the concentration of GPRC5C present in the exosome in the specimen collected from the subject is maintained at a concentration the same as or lower than the concentration of GPRC5C present in the exosome in the specimen collected from the healthy person, it is determined that the possibility of the subject having pancreatic cancer is low.

In addition, as a criteria value for monitoring the possibility of the subject having pancreatic cancer, instead of the concentration of GPRC5C present in the exosome in the specimen collected from a healthy person, a ratio of the concentration of GPRC5C present in the exosome in the specimen collected from the healthy person with respect to the concentration of the exosome-specific antigen can be used. In this case, the ratio of the concentration of GPRC5C present in the exosome in the specimen collected from the subject with respect to the concentration of the exosome-specific antigen is compared with the ratio of the concentration of GPRC5C present in the exosome in the specimen collected from the healthy person with respect to the concentration of the exosome-specific antigen. As the exosome-specific antigen, for example, the above-described exosome-specific antigen and the like are exemplified.

In addition, in step (2D) of measurement method 5, the concentration of GPRC5C present in the exosome in the specimen can be measured by using an exosome isolated from a specimen collected from the subject. Specifically, a method including the following steps is exemplified.

[Measurement Method 6]

(1E) A step of sequentially collecting a specimen from a subject;

(2E) A step of isolating an exosome from the specimen collected in step (1E);

(3E) A step of measuring a concentration of GPRC5C present in the exosome isolated in step (2E);

(4E) A step of determining a concentration of GPRC5C present in an exosome in the specimen from the concentration of GPRC5C measured in step (3E);

(5E) A step of determining that the possibility of the subject having pancreatic cancer is high in a case where the concentration of GPRC5C determined in step (4E) is maintained at a concentration higher than a concentration of GPRC5C present in an exosome in a specimen collected from a healthy person, and determining that the possibility of the subject having pancreatic cancer is low in a case where the concentration of GPRC5C determined in step (4E) is maintained at a concentration the same as or lower than the concentration of GPRC5C present in the exosome in the specimen collected from the healthy person.

<Step (1E)>

In step (1E), as the specimen collected from the subject, the above-described specimen and the like are exemplified.

<Step (2E)>

In step (2E), the method of isolating an exosome is not particularly limited as long as it is a method capable of isolating an exosome in a specimen. For example, the above-described method and the like are exemplified.

<Step (3E)>

As the measurement method of the concentration of GPRC5C present in the exosome in step (3E), any method can be used as long as it is capable of measuring a concentration of GPRC5C present in an exosome. For example, a method such as an immunoassay method can be used. As the measurement method of the concentration of GPRC5C present in the exosome by the immunoassay method, the following aspects are exemplified.

Aspect 1

A method of using an antibody binding to GPRC5C or a fragment of the antibody.

Aspect 2

A method of using an antibody binding to GPRC5C or a fragment of the antibody and an antibody binding to an exosome-specific antigen or a fragment of the antibody.

As the antibody binding to GPRC5C or a fragment of the antibody, for example, the above-described antibody binding to GPRC5C or a fragment of the antibody and the like are exemplified. As the antibody binding to an exosome-specific antigen or a fragment of the antibody, for example, the above-described antibody binding to an exosome-specific antigen or a fragment of the antibody and the like are exemplified.

As the method of Aspect 1, for example, Western blotting and the like are exemplified. As the Western blotting, for example, the above-described method and the like are exemplified.

As the method of Aspect 2, in a case of measuring without disrupting the isolated exosome, the immunoassay method described in measurement method 1, for example, an Exo-Screen method and the like are exemplified, and in a case of measuring by disrupting the isolated exosome, a sandwich ELISA method and the like are exemplified. As the Exo-Screen method, for example, the above-described Exo-Screen method and the like are exemplified.

In the case of measuring without disrupting the isolated exosome, as the antibody binding to GPRC5C or a fragment of the antibody, among the above-described antibody binding to GPRC5C or a fragment of the antibody, an antibody binding to an epitope of GPRC5C present on an exosome surface or a fragment of the antibody is used.

As the method of disrupting the isolated exosome, for example, the above-described method and the like are exemplified.

In the sandwich ELISA method, for example, the antibody binding to GPRC5C or a fragment of the antibody may be used as a solid-phase antibody and the antibody binding to an exosome-specific antigen or a fragment of the antibody may be used as a labeled antibody, and the antibody binding to an exosome-specific antigen or a fragment of the antibody may be used as a solid-phase antibody and the antibody binding to GPRC5C or a fragment of the antibody may be used as a labeled antibody. As the solid phase and the label, for example, known solid phase and label are respectively exemplified. For example, the above-described solid phase and label are respectively used. As a method of preparing the solid-phase antibody and the labeled antibody, for example, a known preparation method is exemplified.

<Step (4E)>

Step (4E) is a step of determining a concentration of GPRC5C in an exosome in the specimen from the concentration of GPRC5C measured in step (3E). The concentration of GPRC5C present in the exosome in the specimen can be determined from the capacity of the specimen and the concentration of GPRC5C measured in step (3E).

<Step (5E)>

Step (5E) is a step of comparing the concentration of GPRC5C present in the exosome in the specimen collected from the subject, determined in step (4E), with the concentration of GPRC5C present in the exosome in the specimen collected from a healthy person. It is determined that the possibility of the subject having pancreatic cancer is high in a case where the concentration of GPRC5C present in the exosome in the specimen collected from the subject is maintained at a concentration higher than a concentration of GPRC5C present in an exosome in a specimen collected from a healthy person, and it is determined that the possibility of the subject having pancreatic cancer is low in a case where the concentration of GPRC5C present in the exosome in the specimen collected from the subject is maintained at a concentration the same as or lower than the concentration of GPRC5C present in the exosome in the specimen collected from the healthy person.

The concentration of GRPC5C present in the exosome in the specimen collected from the healthy person is a criteria value for determining the possibility of the subject having pancreatic cancer, and the concentration of GPRC5C present in the exosome in the specimen collected from the healthy person can be set by measuring concentrations of GPRC5C present in the exosome in the specimen collected from a plurality of healthy persons and statistically analyzing.

As the specimen of the healthy person, the same kind of sample as that of the specimen of the subject is preferable. For example, in a case where the subject's specimen is blood, as the specimen of the healthy person, blood is also preferably used.

As the method of comparing the concentration of GPRC5C present in the exosome of the subject with the concentration of GPRC5C present in the exosome of the healthy person, the above-described method can be used. From the comparison, in a case where the concentration of GPRC5C present in the exosome in the specimen collected from the subject is maintained at a concentration higher than the concentration of GPRC5C present in the exosome in the specimen collected from the healthy person, it is determined that the possibility of the subject having pancreatic cancer is high, and in a case where the where the concentration of GPRC5C present in the exosome in the specimen collected from the subject is maintained at a concentration the same as or lower than the concentration of GPRC5C present in the exosome in the subject collected from the healthy person, it is determined that the possibility of the subject having pancreatic cancer is low.

In addition, as a criteria value for monitoring the possibility of the subject having pancreatic cancer, instead of the concentration of GPRC5C present in the exosome in the specimen collected from the healthy person, a ratio of the concentration of GPRC5C present in the exosome in the specimen collected from the healthy person with respect to the concentration of the exosome-specific antigen can be used. In this case, the ratio of the concentration of GPRC5C present in the exosome in the specimen collected from the subject with respect to the concentration of the exosome-specific antigen is compared with the ratio of the concentration of GPRC5C present in the exosome in the specimen collected from the healthy person with respect to the concentration of the exosome-specific antigen. As the exosome-specific antigen, for example, the above-described exosome-specific antigen and the like are exemplified.

As will be described later in examples, according to the present invention, a pancreatic cancer patient's state such as therapeutic effects after performing operation and decrease in cancer sites can be monitored by measuring a concentration of GPRC5C present in an exosome in a specimen collected from a pancreatic cancer patient from a time before operation to a time after operation.

In addition, according to the present invention, recurrence of pancreatic cancer can be predicted by measuring a concentration of GPRC5C present in an exosome in a specimen collected from a pancreatic cancer patient during treatment.

In addition, according to the present invention, a possibility of a subject having pancreatic cancer can be monitored by measuring a concentration of GPRC5C present in an exosome in a specimen collected from the subject.

4. A Reagent for Examining a Possibility of a Subject Having Pancreatic Cancer

The reagent for examining the possibility of the subject having pancreatic cancer of the present invention is a reagent that contains a reagent for measuring GPRC5C present in an exosome, and can be used in the method of examining the possibility of the subject having pancreatic cancer of the present invention.

In addition, the reagent for examining the possibility of the subject having pancreatic cancer of the present invention may further contain a criteria table that describes criteria in which, in a case where a concentration of GPRC5C present in an exosome in a specimen collected from the subject is higher than a concentration of GPRC5C present in an exosome in a specimen collected from a healthy person, the possibility of the subject having pancreatic cancer is high, and in a case where the concentration of GPRC5C present in the exosome in the specimen collected from the subject is the same as or lower than the concentration of GPRC5C present in the exosome in the specimen collected from the healthy person, the possibility of the subject having pancreatic cancer is low. As criteria described in the criteria table, it is possible to use criteria in which, in a case where a ratio of the concentration of GPRC5C present in the exosome in the specimen collected from the subject with respect to a concentration of an exosome-specific antigen is higher than a ratio of the concentration of GPRC5C present in the exosome in the specimen collected from the healthy person with respect to the concentration of the exosome-specific antigen, the possibility of the subject having pancreatic cancer is high, and in a case where the ratio of the of the concentration of GPRC5C present in the exosome in the specimen collected from the subject with respect to the concentration of an exosome-specific antigen is the same as or lower than a ratio of the concentration of GPRC5C present in the exosome in the specimen collected from the healthy person with respect to the concentration of the exosome-specific antigen, the possibility of the subject having pancreatic cancer is low. As the exosome-specific antigen, for example, the above-described exosome-specific antigen and the like are exemplified.

In the reagent for examining the possibility of the subject having pancreatic cancer of the present invention, the reagent for measuring GPRC5C present in an exosome is a reagent used in the above-described method of measuring GPRC5C present in an exosome. The reagent for measuring GPRC5C present in an exosome is not particularly limited as long as the reagent is capable of measuring GPRC5C present in an exosome in a specimen. For example, an immunoassay reagent and the like are exemplified. As the immunoassay reagent, for example, a reagent based on the above-described immunoassay method and the like are exemplified.

Specific aspects of the reagent for measuring GPRC5C present in an exosome based on the immunoassay method are shown below.

Measurement Reagent 1

A reagent including an antibody binding to GPRC5C or a fragment of the antibody.

Measurement Reagent 2

A reagent including an antibody binding to GPRC5C or a fragment of the antibody to which a label is bonded.

Measurement Reagent 3 A reagent including an antibody binding to GPRC5C or a fragment of the antibody and an antibody binding to an exosome-specific antigen or a fragment of the antibody.

Measurement Reagent 4

A reagent including an antibody binding to GPRC5C or a fragment of the antibody immobilized to a solid phase, and an antibody binding to an exosome-specific antigen or a fragment of the antibody to which a label is bonded.

Measurement Reagent 5

A reagent including an antibody binding to an exosome-specific antigen or a fragment of the antibody immobilized to a solid phase, and an antibody binding to GPRC5C or a fragment of the antibody to which a label is bonded.

Measurement Reagent 6

A reagent including a first antibody binding to GPRC5C or a fragment of the antibody, immobilized to a solid phase, and a second antibody binding to GPRC5C or a fragment of the antibody to which a label is bonded.

As the antibody binding to GPRC5C or a fragment of the antibody and the antibody binding to an exosome-specific antigen or a fragment of the antibody, the above-described antibody binding to GPRC5C or a fragment of the antibody, and the antibody binding to an exosome-specific antigen or a fragment of the antibody are respectively exemplified.

As the label in the antibody binding to GPRC5C or a fragment of the antibody to which a label is bonded, and the antibody binding to an exosome-specific antigen or a fragment of the antibody to which a label is bonded, for example, the above-described label and the like are exemplified. Preparation of the antibody binding to GPRC5C or a fragment of the antibody to which a label is bonded, and the antibody binding to an exosome-specific antigen or a fragment of the antibody to which a label is bonded, can be carried out by a known preparation method of a labeled antibody, for example.

As the solid phase in the antibody binding to GPRC5C or a fragment of the antibody immobilized to a solid phase, and the antibody binding to an exosome-specific antigen or a fragment of the antibody immobilized to a solid phase, the above-described solid phase and the like are exemplified, for example. Immobilization of the antibody binding to GPRC5C or a fragment of the antibody to a solid phase, and immobilization of the antibody binding to an exosome-specific antigen or a fragment of the antibody to a solid phase can be carried out by a known method, for example.

In measurement reagent 6, an epitope to which the first antibody binding to GPRC5C or a fragment of the antibody binds and an epitope to which the second antibody binding to GPRC5C or a fragment of the antibody binds may be different or the same, but being different is preferable.

The measurement reagents 1 to 6 may further contain an exosome isolation reagent. The exosome isolation reagent is not particularly limited as long as it is a reagent capable of isolating an exosome from a specimen. For example, the above-described exosome isolation kit and the like are exemplified.

5. A Reagent for Distinguishing Pancreatic Cancer from a Pancreatic Disease Other than Pancreatic Cancer in a Pancreatic Disease Patient A reagent for distinguishing pancreatic cancer from a pancreatic disease other than pancreatic cancer in a pancreatic disease patient of the present invention is a reagent containing a reagent for measuring GPRC5C present in an exosome, and can be used in the method of distinguishing pancreatic cancer from a pancreatic disease other than pancreatic cancer in a pancreatic disease patient of the present invention.

In addition, the reagent for distinguishing pancreatic cancer from a pancreatic disease other than pancreatic cancer in a pancreatic cancer patient of the present invention may further contain a criteria table in which, in a case where a concentration of GPRC5C present in an exosome in a specimen collected from a pancreatic disease patient is higher than a concentration of GPRC5C present in an exosome in a specimen collected from a patient having a pancreatic disease other than pancreatic cancer, the possibility of pancreatic disease patient having pancreatic cancer is high, and in a case where the concentration of GPRC5C present in the exosome in the specimen collected from the patient having a pancreatic disease is the same as or lower than the concentration of GPRC5C present in the exosome in the specimen collected from the patient having a pancreatic disease other than pancreatic cancer, the possibility of pancreatic disease patient having a pancreatic disease other than pancreatic cancer is high. As the criteria value described in the criteria table, it is possible to use criteria in which, in a case where a ratio of the concentration of GPRC5C present in the exosome in the specimen collected from the pancreatic disease patient with respect to a concentration of the exosome-specific antigen is higher than a ratio of the concentration of GPRC5C present in an exosome in a specimen collected from a healthy person with respect to the concentration of an exosome-specific antigen, the possibility of the subject having pancreatic cancer is high, and in a case where the ratio of the concentration of GPRC5C present in the exosome in the specimen collected from the pancreatic disease patient with respect to a concentration of the exosome-specific antigen is the same as or lower than the ratio of the concentration of GPRC5C present in the exosome in the specimen collected from the healthy person with respect to the concentration of the exosome-specific antigen, the possibility of pancreatic disease patient having a pancreatic disease other than pancreatic cancer is high. As the exosome-specific antigen, the above-described exosome-specific antigen and the like are exemplified, for example.

In the reagent for distinguishing pancreatic cancer from a pancreatic disease other than pancreatic cancer in the pancreatic disease patient of the present invention, the reagent for measuring GPRC5C present in an exosome is a reagent used in the above-described method of measuring GPRC5C present in an exosome. The reagent for measuring GPRC5C present in the exosome is not particularly limited as long as it is capable of measuring GPRC5C present in an exosome in a specimen. For example, an immunoassay reagent and the like are exemplified. As the immunoassay reagent, for example, the above-described reagent based on the immunoassay method and the like are exemplified.

Specific aspects of the reagent for measuring GPRC5C present in an exosome based on the immunoassay method are shown below.

Measurement Reagent 7

A reagent including an antibody binding to GPRC5C or a fragment of the antibody.

Measurement Reagent 8

A reagent including an antibody binding to GPRC5C or a fragment of the antibody to which a label is bonded.

Measurement Reagent 9

A reagent including an antibody binding to GPRC5C or a fragment of the antibody, and an antibody binding to an exosome-specific antigen or a fragment of the antibody.

Measurement Reagent 10

A reagent including an antibody binding to GPRC5C or a fragment of the antibody immobilized to a solid phase, and an antibody binding to an exosome-specific antigen or a fragment of the antibody to which a label is bonded.

Measurement Reagent 11

A reagent including an antibody binding to an exosome-specific antigen or a fragment of the antibody immobilized to a solid phase, and an antibody binding to GPRC5C or a fragment of the antibody to which a label is bonded.

Measurement Reagent 12

A reagent including a first antibody binding to GPRC5C or a fragment of the antibody immobilized to a solid phase, and a second antibody binding to GPRC5C and a fragment of the antibody to which a label is bonded.

As the antibody binding to GPRC5C or a fragment of the antibody, and the antibody binding to an exosome-specific antigen or a fragment of the antibody, the above-described antibody binding to GPRC5C or a fragment of the antibody, and the antibody binding to an exosome-specific antigen or a fragment of the antibody are respectively exemplified.

As the label in the antibody binding to GPRC5C or a fragment of the antibody to which a label is bonded, and the antibody binding to an exosome-specific antigen or a fragment of the antibody to which a label is bonded, the above-described label and the like are exemplified, for example. Preparation of the antibody binding to GPRC5C or a fragment of the antibody to which a label is bonded, and the antibody binding to an exosome-specific antigen or a fragment of the antibody to which a label is bonded can be carried out by a known preparation method of a labeled antibody, for example.

As the solid phase in the antibody binding to GPRC5C or a fragment of the antibody immobilized to a solid phase, and the antibody binding to an exosome-specific antigen or a fragment of the antibody immobilized to a solid phase, the above-described solid phase and the like are exemplified, for example. Immobilization of the antibody binding to GPRC5C or a fragment of the antibody to a solid phase and immobilization of the antibody binding to an exosome-specific antigen or a fragment of the antibody to a solid phase can be carried out by a known method, for example.

In the measurement reagent 12, an epitope to which the first antibody binding to GPRC5C or a fragment of the antibody binds, and an epitope to which the second antibody binding to GPRC5C or a fragment of the antibody binds may be different or the same, but being different is preferable.

The measurement reagents 7 to 12 may further contain an exosome isolation reagent. The exosome isolation reagent is not particularly limited as long as it is a reagent capable of isolating an exosome from a specimen. For example, the above-described exosome isolation reagent and the like are exemplified.

6. A Reagent for Monitoring a Possibility of a Subject Having Pancreatic Cancer

The reagent for monitoring the possibility of the subject having pancreatic cancer of the present invention is a reagent containing a reagent for measuring GPRC5C present in an exosome, and can be used in the method of monitoring the possibility of the subject having pancreatic cancer of the present invention.

In addition, the reagent for monitoring the possibility of the subject having pancreatic cancer may further contain a criteria table that describes criteria in which, in a case where a concentration of GPRC5C present in an exosome in a specimen sequentially collected from the subject is maintained at a concentration higher than a concentration of GPRC5C present in an exosome in a specimen collected from a healthy person, the possibility of the subject having pancreatic cancer is high, and in a case where the concentration of GPRC5C present in the exosome in the specimen sequentially collected from the subject is maintained at a concentration the same as or lower than the concentration of GPRC5C present in the exosome in the specimen collected from the healthy person, the possibility of the subject having pancreatic cancer is low. As criteria described in the criteria table, it is possible to use criteria in which, in a case where a ratio of the concentration of GPRC5C present in the exosome in the specimen collected from the subject with respect to a concentration of an exosome-specific antigen is higher than a ratio of the concentration of GPRC5C present in the exosome in the specimen collected from the healthy person with respect to the concentration of the exosome-specific antigen, the possibility of the subject having pancreatic cancer is high, and in a case where the ratio of the of the concentration of GPRC5C present in the exosome in the specimen collected from the subject with respect to the concentration of an exosome-specific antigen is the same as or lower than a ratio of the concentration of GPRC5C present in the exosome in the specimen collected from the healthy person with respect to the concentration of the exosome-specific antigen, the possibility of the subject having pancreatic cancer is low. As the exosome-specific antigen, for example, the above-described exosome-specific antigen and the like are exemplified.

In the reagent for monitoring the possibility of the subject having pancreatic cancer of the present invention, the reagent for measuring GPRC5C present in an exosome is a reagent used in the above-described method of measuring GPRC5C present in the exosome. The reagent for measuring GPRC5C present in the exosome is not particularly limited as long as it is a reagent capable of measuring GPRC5C present in an exosome in a specimen. For example, an immunoassay reagent and the like are exemplified. As the immunoassay reagent, for example, the above-described reagent based on the immunoassay method is exemplified.

Specific aspects of the reagent for measuring GPRC5C present in the exosome based on the immunoassay method are shown below.

Measurement Reagent 13

A reagent including an antibody binding to GPRC5C or a fragment of the antibody.

Measurement Reagent 14

A reagent including an antibody binding to GPRC5C or a fragment of the antibody to which a label is bonded.

Measurement Reagent 15

A reagent including an antibody binding to GPRC5C or a fragment of the antibody, and an antibody binding to an exosome-specific antigen or a fragment of the antibody.

Measurement Reagent 16

A reagent including an antibody binding to GPRC5C or a fragment of the antibody immobilized to a solid phase, and an antibody binding to an exosome-specific antigen or a fragment of the antibody to which a label is bonded.

Measurement Reagent 17

A reagent including an antibody binding to an exosome-specific antigen or a fragment of the antibody immobilized to a solid phase, and an antibody binding to GPRC5C or a fragment of the antibody to which a label is bonded.

Measurement Reagent 18

A reagent including a first antibody binding to GPRC5C or a fragment of the antibody immobilized to a solid phase, and a second antibody binding to GPRC5C or a fragment of the antibody to which a label is bonded.

As the antibody binding to GPRC5C or a fragment of the antibody, and the antibody binding to an exosome-specific antigen or a fragment of the antibody, the above-described antibody binding to GPRC5C or a fragment of the antibody, and the antibody binding to an exosome-specific antigen or a fragment of the antibody and the like are respectively exemplified.

As the label in the antibody binding to GPRC5C or a fragment of the antibody to which a label is bonded, and the antibody binding to an exosome-specific antigen or a fragment of the antibody to which a label is bonded, for example, the above-described label and the like are exemplified. Preparation of the antibody binding to GPRC5C or a fragment of the antibody to which a label is bonded, and the antibody binding to an exosome-specific antigen or a fragment of the antibody to which a label is bonded can be carried out by a known preparation method of a labeled antibody, for example.

As the solid phase in the antibody binding to GPRC5C or a fragment of the antibody immobilized to a solid phase, and the antibody binding to an exosome-specific antigen or a fragment of the antibody immobilized to a solid phase, for example, the above-described solid phase and the like are exemplified. Immobilization of the antibody binding to GPRC5C or a fragment of the antibody to a solid phase and immobilization of the antibody binding to an exosome-specific antigen or a fragment of the antibody to a solid phase can be carried out by a known method, for example. In the measurement reagent 18, an epitope to which the first antibody binding to GPRC5C or a fragment of the antibody, and an epitope to which the second antibody binding to GPRC5C or a fragment of the antibody may be different or the same, but being different is preferable.

The measurement reagents 13 to 18 may further contain an exosome isolation reagent. The exosome isolation reagent is not particularly limited as long as it is a reagent capable of isolating an exosome from a specimen. For example, the above-described exosome isolation kit and the like are exemplified.

7. Pancreatic Cancer Marker

A pancreatic cancer marker of the present invention includes GPRC5C or a GPRC5C gene. The accession number of GenBank of human GPRC5C is NP_071319.2; NP_061123.3. In addition, the accession number of GenBank of mRNA of human GPRC5C is NM_022036.2; NM_018653.3.

8. A Pancreatic Cancer Diagnosis Reagent

A pancreatic cancer diagnosis reagent of the present invention includes a specific binding substance to GPRC5C, a primer set capable of amplifying a GPRC5C gene, or a probe specifically hybridized to mRNA of a GPRC5C gene.

(Specific Binding Substance)

As the specific binding substance, an antibody binding to GPRC5C, a fragment of the antibody, an aptamer binding to GPRC5C, and the like are exemplified. As the antibody or a fragment of the antibody, the above-described ones are exemplified.

The aptamer is a substance having a specific binding ability to a target substance. As the aptamer, a nucleic acid aptamer, a peptide aptamer, and the like are exemplified. A nucleic acid aptamer having a specific binding ability to a target substance can be selected by a method of systematic evolution of ligand by exponential enrichment (SELEX) and the like, for example. In addition, a peptide aptamer having a specific binding ability to a target peptide can be selected by a Two-hybrid method using yeast and the like, for example.

(Primer Set)

The primer set capable of amplifying a GPRC5C gene is not particularly limited as long as it is capable of amplifying mRNA of the gene by an RT-PCR method and the like.

mRNA of the gene has a base sequence described in the GenBank database specified by the above-described accession number. Since there is a case where a splicing variant and the like are present in mRNA, mRNA of the gene is not limited to the one specified by the above-described accession number.

For example, mRNA of a GPRC5C gene in a sample can be detected by performing RT-PCR using this primer set using a tissue of the subject and the like as the sample.

(Probe)

The probe is not particularly limited as long as it is specifically hybridized to mRNA of a GPRC5C gene. The probe may be immobilized to a carrier to constitute a DNA microarray and the like. For example, whether or not the subject has pancreatic cancer can be determined by contacting mRNA extracted from the tissue of the subject with the DNA microarray and detecting mRNA of the GPRC5C gene hybridized to the probe. As the carrier, for example, the above-described carrier and the like are exemplified.

9. A Method of Determining a Biological Sample

A method of determining a biological sample of the present invention includes a step of measuring an amount of GPRC5C in a biological sample and a step of determining that the biological sample is collected from a pancreatic cancer patient in a case where the measured amount of GPRC5C is larger than that of a control.

Whether or not the biological sample is collected from a pancreatic cancer patient can be determined by the determination method of the present invention. According to the determination method of the present invention, pancreatic cancer can be specifically detected.

In the determination method of the present invention, the biological sample may be plasma, blood serum, or an exosome purified from plasma or blood serum, as described above. The step of measuring GPRC5C in the biological sample can be carried out by detection using sandwich ELISA, Western blotting, and reversed-phase protein array, and by immunohistochemical staining, using the above-described specific binding substance.

Here, the measured GPRC5C may be converted into a quantitative value based on a calibration curve prepared by using serially diluted GPRC5C with a known concentration as a standard In the determination method of the present invention, in a case where the amount of GPRC5C in the biological sample is larger than the amount of GPRC5C in a control sample, it is determined that the biological sample is collected from a pancreatic cancer patient. As the control, a biological sample collected from a healthy person or a patient having a pancreatic disease other than pancreatic cancer is exemplified. Or, in a case where a criteria value is set based on the amount of GPRC5C present in the biological sample collected from a healthy person in advance, and the amount of GPRC5C is larger than the criteria value, it may be determined that the biological sample is collected from a pancreatic cancer patient.

The determination method of the present invention may include a step of measuring an expression amount of a GPRC5C gene in a biological sample and a step of determining that the biological sample is collected from a pancreatic cancer patient in a case where the measured expression amount of the gene is larger than that of a control.

In the determination method of the present invention, the biological sample may be a tissue of the subject and the like. The step of measuring the expression amount of a GPRC5C gene in the biological sample can be carried out by RT-PCR, quantitative RT-PCR using the above-described primer set, and the like. Or, the expression amount of a GPRC5C gene may be measured by DNA microarray analysis, Northern blotting using the above-described probe, and the like. Here, the measured expression amount of the GPRC5C gene may be converted into a quantitative value based on a calibration curve prepared by using a serially diluted fragment of each gene with a known concentration and the like as a standard.

In addition, in the determination method of the present invention, in a case where the expression amount of the GPRC5C gene in the biological sample is larger than the expression amount of the gene in the control sample, it is determined that the biological sample is collected from a pancreatic cancer patient. As the control, for example, a biological sample collected from a healthy person or a patient having a pancreatic disease other than pancreatic cancer and the like are exemplified. Or, in a case where a criteria value is set based on the expression amount of the GPRC5C gene in the biological sample collected from a healthy person in advance, and the expression amount of the gene is larger than the criteria value, it may be determined that the biological sample is collected from a pancreatic cancer patient.

EXAMPLES

Hereinafter, the present invention will be described using examples, but the present invention is not limited to the examples.

Example 1

Detection of GRPC5C present in an exosome in each blood serum Blood serum (4 specimens) collected from healthy persons, blood serum (4 specimens) collected from pancreatitis patients, and blood serum (4 specimens: two kinds of stage IIA, one kind of stage IIB, and one kind of stage III) collected from pancreatic cancer patients were subjected to ultracentrifugation for 70 minutes in a swing rotor at 100,000×g or greater (4° C.), the supernatant was discarded, PBS [10 mmol/L phosphoric buffer solution (pH 7.2) containing 0.15 mol/L sodium chloride] was added thereto and precipitated, and the precipitated fraction was used as an exosome fraction. The exosome fraction was dissolved in PBS (total amount 100 µL). The exosome fraction solution equivalent to 100 µL blood serum per well was added and mixed with 4×sample buffer (0.125 mol/L Tris buffer solution containing 4% dodecyl sodium sulfate, 10% sucrose, 0.01% bromophenol blue, 10% 2-mercaptoethanol [pH 6.8]) of ⅓ amount of the solution, kept warm at 95° C. for 5 minutes, and then ice-cooled. The treatment solution was applied to a well of 4-15% Mini-PROTEAN TGX gel (manufactured by Bio-Rad), and SDS-PAGE was performed. The gel after SDS-PAGE was transferred to a PVDF membrane, and the membrane was subjected to blocking at room temperature (25° C.) for 1 hour by using a Nacalai Blocking One solution [manufactured by Nacalai Tesque, inc.]. Subsequently, primary antibody reaction was carried out at room temperature (25° C.) for 1 hour (Anti-GPRC5C antibody C-terminal Rabbit polyclonal [manufactured by Abcam Corporation] 1:500). Subsequently, a secondary antibody reaction was carried out at room temperature (25° C.) for 1 hour (Rabbit IgG HRP [manufactured by GE Healthcare] 1:5000). Finally, a color reaction (room temperature [25° C.], 5 minutes) was carried out by using ImmunoStar LD (Wako Pure Chemical Industries, Ltd), and a blotting image was captured to detect a signal of GPRC5C present in an exosome in each blood serum. The result of the blotting image is shown in FIG. 1.

In addition, according to the method, an expression amount of CD63 present in an exosome in each blood serum was evaluated by Western blotting, using Purified Mouse Anti-Human CD63 (manufactured by Becton Dickinson Japan, clone: H5C6). The result is shown in FIG. 1.

As is apparent from FIG. 1, it was evident that in comparison between the healthy person and the pancreatic cancer patient, GPRC5C present in an exosome is remarkably highly expressed in the pancreatic cancer patient.

Example 2

In order to compare concentrations of GPRC5C present in exosomes in blood serum by using blood serum (10 specimens) collected from healthy persons, blood serum (10 specimens) collected from pancreatitis patients, and blood serum (23 specimens) collected from pancreatic cancer patients, a signal of GPRC5C and a signal of CD63 present in an exosome in blood serum were detected as a concentration of GPRC5C and a concentration of CD63 present in the exosome, according to the method of Example 1. The signal ratio of GPRC5C/CD63 is shown in FIG. 2.

Figure 2:
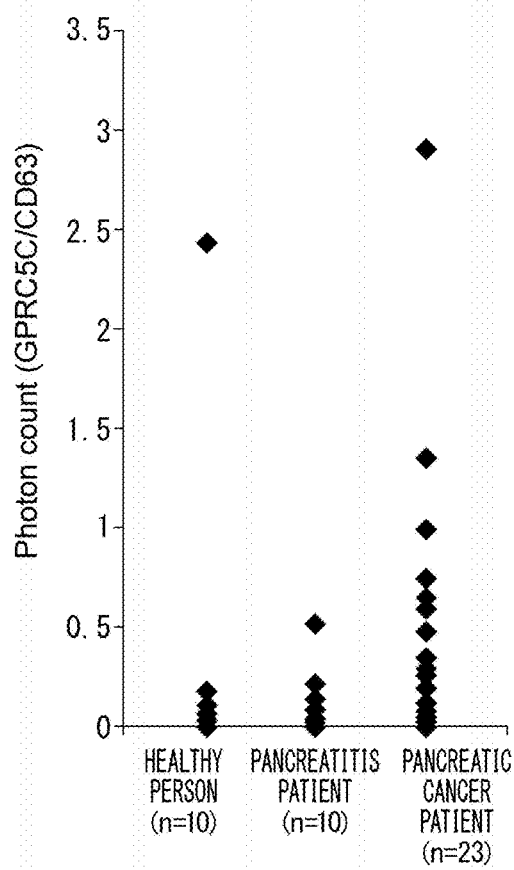
FIG. 2 shows the results of comparing concentrations of GPRC5C present in exosomes in each blood serum collected from healthy persons (10 specimens), pancreatitis patients (10 specimens), and pancreatic cancer patients (23 specimens). The axis of ordinates indicates a signal ratio of GPRC5C/CD63, calculated from a signal of GPRC5C and a signal of CD63 obtained by Western blotting.

As is apparent from FIG. 2, it was evident that, compared to the concentration of GPRC5C present in an exosome in the blood serum collected from healthy persons, the concentration of GPRC5C present in an exosome in the blood serum collected from pancreatic cancer patients is higher. In addition, it was evident that, compared to the concentration of GPRC5C present in an exosome in the blood serum collected from pancreatitis patients, the concentration of GPRC5C present in an exosome in the blood serum collected from pancreatic cancer patients is higher.

Example 3

Regarding pancreatic cancer patients (5 cases), concentrations of GPRC5C present in exosomes in blood serum before operation and after operation were compared by using Western blotting, according to the method of Example 1. The result of blotting images is shown in FIG. 3.

Figure 3:
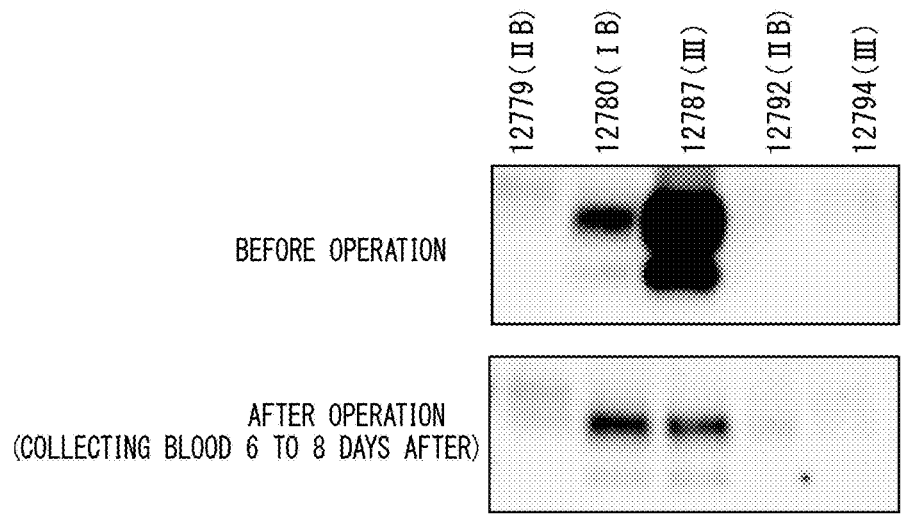
FIG. 3 shows the results of detecting GPRC5C (48 kD) by Western blotting by using exosomes in blood serum collected from pancreatic cancer patients (stage IB: 1 specimen, stage IIB: 2 specimens, stage III: 2 specimens) before operation and after operation.

As is apparent from FIG. 3, it was evident that, compared to before operation, the concentration of GPRC5C present in an exosome is remarkably decreased after operation.

Example 4

A concentration of GPRC5C present in an exosome in blood serum collected from a recurrent pancreatic cancer patient and a concentration of GPRC5C present in an exosome in blood serum collected from a healthy person were measured by the method of Example 1 using Western blotting, and both concentrations of GPRC5C were compared to each other. In addition, at the same time, a concentration of CD9 present in an exosome in each blood serum was measured by Western blotting, using a biotinized anti-CD9 antibody (1,000 times diluted) obtained by biotinizing an anti-CD9 antibody (8A12) (manufactured by Cosmo Bio Co., Ltd) and HRP-binding streptoavidin (manufactured by CST Corporation) (2,000 times diluted). From the measured concentration of GPRC5C and concentration of CD9, a ratio of the concentration of GPRC5C to the concentration of CD9 was calculated, and used as a signal ratio of GPRC5C/CD9. The signal ratio of GPRC5C/CD9 is shown in FIG. 4.

Figure 4:
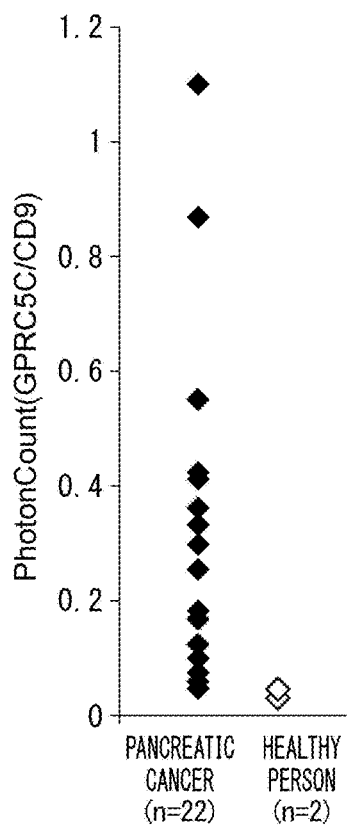
FIG. 4 shows the results of comparing concentrations of GPRC5C present in exosomes in each blood serum by using exosomes in blood serum collected from recurrent pancreatic cancer patients (22 specimens) and healthy persons (2 specimens). The axis of ordinates indicates a signal of GPRC5C/CD9, calculated from a signal of GPRC5C and a signal of CD9 obtained by Western blotting.

As is apparent from FIG. 4, it was evident that, compared to the concentration of GPRC5C present in an exosome in the blood serum collected from the healthy person, the concentration of GPRC5C present in an exosome in the blood serum collected from the recurrent pancreatic cancer patient is higher.

INDUSTRIAL APPLICABILITY

The method and the reagent for examining a possibility of a subject having pancreatic cancer, the method and the reagent for distinguishing pancreatic cancer from a pancreatic disease other than pancreatic cancer, the method and the reagent for monitoring a possibility of a subject having pancreatic cancer, a pancreatic cancer marker, a pancreatic cancer diagnosis reagent, and a method of determining biological sample of the present invention are useful for clinical diagnosis.

The invention claimed is:

1. A method of examining a subject for pancreatic cancer, comprising:
   measuring a concentration of GPRC5C (G protein-coupled receptor family C group 5 member C) present in an exosome in blood collected from the subject having pancreatic cancer before performing treatment on the subject by using an immunoassay method;
   measuring a concentration of GPRC5C present in an exosome in blood collected from the subject after performing the treatment on the subject; and
   monitoring a therapeutic effect after performing the treatment on the subject and a decrease in cancer sites of the pancreatic cancer of the subject based on the measuring of the concentration of GPRC5C present in the exosome in blood collected from the subject having pancreatic cancer before performing the treatment and after performing the treatment on the subject,
   wherein the immunoassay method is carried out by using an antibody binding to GPRC5C or a fragment of the antibody and an antibody binding to an antigen specifically expressed in an exosome-specific antigen or a fragment of the antibody, and
   wherein the exosome-specific antigen is CD63, CD9, CD81, CD37, CD53, CD82, CD13, CD11, CD86, ICAM-1 (intercellular adhesion molecule-1), Rab5, Annexin V, or LAMP1 (lysosome-associated membrane protein 1).

2. The method according to claim 1,
   wherein measuring the concentration of GPRC5C present in the exosome in the blood collected from the subject is carried out by using an exosome isolated from the blood.

3. A method of monitoring a subject for pancreatic cancer, comprising:
   measuring at least twice consecutively a concentration of GPRC5C (G protein-coupled receptor family C group 5 member C) present in an exosome in blood collected from the subject having pancreatic cancer before performing treatment on the subject by using an immunoassay method; and
   measuring a concentration of GPRC5C present in an exosome in blood collected from the subject after performing the treatment on the subject; and
   monitoring a therapeutic effect after performing the treatment on the subject and a decrease in cancer sites of the pancreatic cancer of the subject based on the measured concentration of GPRC5C present in the exosome in the blood collected from the subject having pancreatic cancer before performing the treatment and after performing the treatment on the subject,
   wherein the immunoassay method is carried out by using an antibody binding to GPRC5C or a fragment of the antibody and an antibody binding to an antigen specifically expressed in an exosome-specific antigen or a fragment of the antibody, and
   wherein the exosome-specific antigen is CD63, CD9, CD81, CD37, CD53, CD82, CD13, CD11, CD86, ICAM-1 (intercellular adhesion molecule-1), Rab5, Annexin V, or LAMP1 (lysosome-associated membrane protein 1).

4. The method according to claim 3,
   wherein measuring of the concentration of GPRC5C present in the exosome in the blood collected from the subject is carried out by using an exosome isolated from the blood.

5. The method according to claim 1, further comprising:
   collecting the blood from the subject having pancreatic cancer before performing the treatment on the subject; and
   collecting the blood from the subject having pancreatic cancer after performing the treatment on the subject.

6. The method according to claim 3, further comprising:
   collecting the blood from the subject having pancreatic cancer before performing the treatment on the subject; and
   collecting the blood from the subject having pancreatic cancer after performing the treatment on the subject.

* * * * *